US011342068B2

(12) United States Patent
Levings et al.

(10) Patent No.: US 11,342,068 B2
(45) Date of Patent: May 24, 2022

(54) SELF-OPTIMISING RESPIRATORY THERAPY SYSTEM

(71) Applicant: ResMed Inc., San Diego, CA (US)

(72) Inventors: Robert Andrew Levings, Halifax (CA); Mark David Buckley, Sydney (AU); Michael Waclaw Colefax, Sydney (AU); Susan Robyn Lynch, Maitland (AU); Rajwant Sodhi, Halifax (CA)

(73) Assignee: ResMed Inc., San Diego, CA (US)

( * ) Notice: Subject to any disclaimer, the term of this patent is extended or adjusted under 35 U.S.C. 154(b) by 0 days.

(21) Appl. No.: 15/500,431

(22) PCT Filed: Jul. 31, 2015

(86) PCT No.: PCT/US2015/043204
§ 371 (c)(1),
(2) Date: Jan. 30, 2017

(87) PCT Pub. No.: WO2016/019292
PCT Pub. Date: Feb. 4, 2016

(65) Prior Publication Data
US 2017/0209657 A1 Jul. 27, 2017

Related U.S. Application Data

(60) Provisional application No. 62/031,975, filed on Aug. 1, 2014.

(51) Int. Cl.
*G16H 40/00* (2018.01)
*A61M 16/00* (2006.01)
(Continued)

(52) U.S. Cl.
CPC ........ *G16H 40/00* (2018.01); *A61M 16/0051* (2013.01); *A61M 16/0066* (2013.01);
(Continued)

(58) Field of Classification Search
CPC ........ G16H 10/00; G16H 10/20; G16H 15/00; G16H 20/00; G16H 20/30; G16H 20/70;
(Continued)

(56) References Cited

U.S. PATENT DOCUMENTS

| 4,944,310 | A | 7/1990 | Sullivan |
| 5,931,160 | A | 8/1999 | Gilmore et al. |

(Continued)

FOREIGN PATENT DOCUMENTS

| WO | 2013020167 A1 | 2/2013 |
| WO | 2013033419 A1 | 3/2013 |

(Continued)

OTHER PUBLICATIONS

Wikipeia article, Weight Function, Mar. 3, 2019, 4 pages.*

(Continued)

*Primary Examiner* — Jason S Tiedeman
(74) *Attorney, Agent, or Firm* — Botos Churchill IP Law LLP

(57) ABSTRACT

Methods or systems (7000) are implemented for treatment with or monitoring use of respiratory pressure therapy device(s). The device may be for a respiratory disorder. A processor, such as a processor of a server communicating with the therapy device, may analyse data relating to respiratory therapy delivered by the device. The processor may generate data in the processor representing a prediction, such as compliance prediction(s), about progress of therapy based on the analysis. The processor may select an action to improve therapy based on data representing the prediction. The processor may take or prompt selected action to improve the therapy. In some cases, a processor may analyse usage data concerning a period of days with a therapy device and generate compliance prediction indicators based on the analysis. The indicators indicate whether compliance will be (Continued)

likely. The processor may recommend engagement action to improve compliance based on evaluation of the indicators.

22 Claims, 15 Drawing Sheets

(51) Int. Cl.
| | |
|---|---|
| *A61M 16/16* | (2006.01) |
| *G16H 20/40* | (2018.01) |
| *G16H 40/67* | (2018.01) |
| *A61M 16/06* | (2006.01) |
| *A61M 16/10* | (2006.01) |

(52) U.S. Cl.
CPC .......... *A61M 16/026* (2017.08); *A61M 16/06* (2013.01); *A61M 16/16* (2013.01); *G16H 20/40* (2018.01); *G16H 40/67* (2018.01); *A61M 16/0633* (2014.02); *A61M 16/0683* (2013.01); *A61M 16/0694* (2014.02); *A61M 16/105* (2013.01); *A61M 2016/003* (2013.01); *A61M 2016/0027* (2013.01); *A61M 2202/0208* (2013.01); *A61M 2205/3584* (2013.01); *A61M 2205/50* (2013.01); *A61M 2205/505* (2013.01); *A61M 2205/52* (2013.01); *Y02A 90/10* (2018.01)

(58) Field of Classification Search
CPC ........ G16H 40/00; G16H 40/60; G16H 40/63; G06Q 50/22; G06Q 50/24; G06F 19/30; G06F 19/32; G06F 19/34; G06F 19/3456; G06F 19/3481; G06F 19/36; G06F 19/325
USPC ....................................................... 705/2, 3
See application file for complete search history.

(56) References Cited

U.S. PATENT DOCUMENTS

| | | | |
|---|---|---|---|
| 6,039,688 A | 3/2000 | Douglas et al. | |
| 6,299,581 B1 | 10/2001 | Rapoport et al. | |
| 6,532,959 B1 | 3/2003 | Berthon-Jones | |
| 7,866,944 B2 | 1/2011 | Kenyon et al. | |
| 8,333,696 B2* | 12/2012 | Levendowski | A61B 5/0002 600/300 |
| 8,528,551 B2 | 9/2013 | Mulcahy et al. | |
| 8,636,479 B2 | 1/2014 | Kenyon et al. | |
| 8,638,014 B2 | 1/2014 | Sears et al. | |
| 8,666,926 B1* | 3/2014 | Nease | G06F 19/3456 706/50 |
| 9,463,294 B2* | 10/2016 | Laura Lapoint | A61M 16/024 |
| 2003/0208465 A1 | 11/2003 | Yurko et al. | |
| 2003/0236450 A1* | 12/2003 | Kocinski | G16H 40/63 600/300 |
| 2006/0130836 A1 | 6/2006 | Wixey et al. | |
| 2008/0059224 A1* | 3/2008 | Schechter | G16H 10/60 705/2 |
| 2008/0109252 A1* | 5/2008 | LaFountain | G16H 20/10 705/2 |
| 2008/0114689 A1 | 5/2008 | Psynik et al. | |
| 2008/0161651 A1* | 7/2008 | Peterson | G06F 19/3418 600/300 |
| 2009/0125328 A1* | 5/2009 | Nevins | G06Q 50/24 705/3 |
| 2010/0049008 A1* | 2/2010 | Doherty | A61B 5/0476 600/301 |
| 2010/0170513 A1 | 7/2010 | Bowditch et al. | |
| 2011/0112857 A1 | 5/2011 | Yurko et al. | |
| 2011/0184250 A1* | 7/2011 | Schmidt | G06Q 10/00 600/300 |
| 2011/0192400 A9 | 8/2011 | Burton et al. | |
| 2011/0199214 A1 | 8/2011 | Gawlick | |
| 2011/0295083 A1 | 12/2011 | Doelling et al. | |
| 2012/0072238 A1 | 3/2012 | Collins, Jr. et al. | |
| 2012/0145152 A1* | 6/2012 | Lain | A61B 5/08 128/204.23 |
| 2012/0215081 A1* | 8/2012 | Euliano | A61B 5/037 600/323 |
| 2012/0240933 A1* | 9/2012 | Haas | A61M 16/06 128/204.21 |
| 2013/0054215 A1* | 2/2013 | Stubna | G16Z 99/00 703/11 |
| 2013/0340758 A1* | 12/2013 | Schindhelm | A61B 5/087 128/204.23 |
| 2014/0048072 A1* | 2/2014 | Angelico | A61M 16/0063 128/204.23 |
| 2014/0129249 A1* | 5/2014 | Nkoy | G16H 50/30 705/2 |
| 2014/0164017 A1* | 6/2014 | Merkin | G16H 40/60 705/3 |
| 2014/0278513 A1* | 9/2014 | Prakash | G06Q 30/0601 705/2 |
| 2015/0154380 A1* | 6/2015 | Duckworth | G06F 19/3481 705/2 |
| 2015/0174347 A1* | 6/2015 | Kirby | A61M 16/024 128/204.23 |
| 2015/0186602 A1* | 7/2015 | Pipke | A61B 5/0022 705/3 |
| 2015/0332012 A1* | 11/2015 | Edelson | G16H 50/30 705/2 |
| 2016/0106339 A1* | 4/2016 | Behzadi | A61B 5/0022 600/302 |

FOREIGN PATENT DOCUMENTS

| | | |
|---|---|---|
| WO | 2013187776 A1 | 12/2013 |
| WO | 2014013411 A1 | 1/2014 |

OTHER PUBLICATIONS

John B. West, Respiratory Physiology: The Essentials, Lippincott Williams & Wilkins, 9th Edition, published Sep. 21, 2011.
International Search Report and Written Opinion for Application No. PCT/US2015/043204 dated Oct. 26, 2015.
International Search Report and Written Opinion for Application No. PCT/US2015/043226 dated Dec. 30, 2015.
Extended European Search Report and Written Opinion in EP15828142 dated Mar. 1, 2018.
Extended European Search Report and Written Opinion for EP15827493.6 dated Apr. 13, 2018.
ResTraxx System User Guide, ResMed Limited, Jan. 2, 2008. Retrieved from the Internet: http://manualzz.com/doc/7495030/restraxx%E2%84%A2-system-apria-healthcare [retrieved Mar. 29, 2018].
Stepnowsky Jr. et al., "Pilot Randomized Trial of the Effect of Wireless Telemonitoring on Compliance and Treatment Efficacy in Obstructive Sleep Apnea," Journl of Medical Internet Research, Apr.-Jun. 2007, vol. 9(4), pp. 1-22 (published onl;ine May 17, 2007).
Stepnowsky CJ, Marler MR, Ancoli-Israel S. Determinants of nasal CPAP compliance. Sleep medicine. May 1, 2002;3(3):239 47.
EP Communication dated Jan. 31, 2020, EP Application No. 15828142.8.
Dipansu, Ghosh, et al., ""Identifying poor compliance with CPAP in obstructive sleep apnoea: A simpleprediction equation using data after a two week trial"", Respiratory Medicine, Bailliere Tindall, London, GB, vol. 107, No. 6, Nov. 10, 2012 (Nov. 10, 2012), pp. 936-942, XP028583565, ISSN: 0954-6111, DOI: 10.1016/J.RMED. 2012.10.008.

* cited by examiner

SELF-OPTIMISING RESPIRATORY THERAPY SYSTEM

1 CROSS-REFERENCE TO RELATED APPLICATIONS

The present application is a national phase entry under 35 U.S.C. § 371 of International Application No. PCT/US2015/043204, filed Jul. 31, 2015, published in English, which claims the benefit of U.S. Provisional Application No. 62/031,975, filed Aug. 1, 2014, all of which is hereby incorporated herein by reference.

2 STATEMENT REGARDING FEDERALLY SPONSORED RESEARCH OR DEVELOPMENT

Not Applicable

3 THE NAMES OF PARTIES TO A JOINT RESEARCH DEVELOPMENT

Not Applicable

4 SEQUENCE LISTING

Not Applicable

5 BACKGROUND OF THE TECHNOLOGY 5.1 Field of the Technology

The present technology relates to one or more of the detection, diagnosis, treatment, prevention and amelioration of respiratory-related disorders. In particular, the present technology relates to medical devices, and their use.

5.2 Description of the Related Art 5.2.1 Human Respiratory System and its Disorders The respiratory system of the body facilitates gas exchange.

The nose and mouth form the entrance to the airways of a patient. The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist. Certain disorders may be characterised by particular events, e.g. apneas, hypopneas, and hyperpneas.

Obstructive Sleep Apnea (OSA), a form of Sleep Disordered Breathing (SDB), is characterized by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterised by repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production. A COPD exacerbation is a sudden worsening of the condition of a COPD patient necessitating some kind of intervention.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

A range of therapies have been used to treat or ameliorate such conditions. Furthermore, otherwise healthy individuals may take advantage of such therapies to prevent respiratory disorders from arising.

5.2.2 Respiratory Therapies

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion by pushing the soft palate and tongue forward and away from the posterior oropharyngeal wall. Treatment of OSA by CPAP therapy may be voluntary, and hence patients may elect not to persevere with therapy if they find devices used to provide such therapy uncomfortable, difficult to use, expensive, or aesthetically unappealing.

Non-invasive ventilation (NIV) provides ventilatory support to a patient through the upper airways to assist the patient in taking a full breath and/or maintain adequate oxygen levels in the body by doing some or all of the work of breathing. The ventilatory support is provided via a patient interface. NIV has been used to treat CSR, OHS, COPD, NMD and Chest Wall disorders.

Invasive ventilation (IV) provides ventilatory support to patients that are no longer able to effectively breathe themselves and may be provided using a tracheostomy tube.

5.2.3 Diagnosis and Therapy Systems

These therapies may be provided by a therapy system. Therapy systems, suitably modified, may also be used to diagnose a condition without treating it.

A therapy system may comprise a Respiratory Pressure Therapy Device (RPT device), an air circuit, a humidifier, a patient interface, and data management.

5.2.3.1 Patient Interface

A patient interface may be used to interface respiratory equipment to its user, for example by providing a flow of air. The flow of air may be provided via a mask to the nose and/or mouth, a tube to the mouth or a tracheostomy tube to the trachea of the user. Depending upon the therapy to be applied, the patient interface may form a seal, e.g. with a face region of the patient, to facilitate the delivery of air at a pressure at sufficient variance with ambient pressure to effect therapy, e.g. a positive pressure of about 10 $cmH_2O$. For other forms of therapy, such as the delivery of oxygen, the patient interface may not include a seal sufficient to facilitate delivery to the airways of a supply of air at a positive pressure of about 10 $cmH_2O$.

5.2.3.2 Respiratory Pressure Therapy (RPT) Device

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even RPT devices designed for medical treatment may suffer from shortcomings, including one or more of comfort, noise, ease of use, efficacy, size, weight, manufacturability, cost, and reliability.

5.2.3.3 Humidifier

Delivery of a flow of air without humidification may cause drying of airways. The use of a humidifier with a RPT device and the patient interface produces humidified air that minimizes drying of the nasal mucosa and increases patient airway comfort. In addition in cooler climates, warm air applied generally to the face area in and about the patient interface is more comfortable than cold air. A range of artificial humidification devices and systems are known, however they may not fulfil the specialised requirements of a medical humidifier.

5.2.3.4 Data Management

Insurance companies, or other reimbursing entities, often require evidence that the patient prescribed with respiratory therapy has been "compliant", that is, has used their RPT device according to a predetermined "compliance rule" before reimbursing the patient for the RPT device. Compliance rules generally require some minimum amount of usage per session for some fraction of a number of consecutive sessions known as the compliance period. One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over the time period specified in the compliance rule, and compare with the compliance rule. Once the health care provider has determined that the patient has used their RPT device according to the compliance rule, the health care provider may notify the reimbursing entity that the patient is compliant. This process can be costly, time-consuming, and error-prone if conducted manually. RPT devices typically therefore contain data management capability that enables the device to store and transmit therapy variable data to a remote server to determine whether the patient has used the RPT device according to the compliance rule.

5.2.3.5 Compliance Problems

Studies have shown that up to 90% of patients prescribed with CPAP therapy have at least some problems meeting compliance rules. Difficulty in setting up an RPT device, discomfort due to an ill-fitting or ill-adjusted patient interface, lack of tolerance for the sensation of positive airway pressure at the prescribed level, excessive leaks causing noise or disruption to the patient or their bed partner, and lack of improvement in subjective well-being are all examples of such problems. Many patients simply give up after early difficulties, and some may seek assistance from their health care provider. Such "engagements" with the patient may, or may not, depending on the skill and knowledge of the health care provider, improve the chances of a patient becoming compliant. Even those patients who are initially compliant may not persist with therapy due to a lack of subjective improvement in their condition. In principle, there is a combination or "therapy program" of device settings, patient interface selection and adjustment, and engagement that maximises the chances of a given patient becoming compliant. However, arriving at such an "optimal" therapy program for each individual patient is currently a labour-intensive, hit-or-miss proposition at best.

6 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to systems used in the diagnosis, amelioration, treatment or prevention of a respiratory disorder.

Another aspect of the present technology relates to methods used in the diagnosis, amelioration, treatment or prevention of a respiratory disorder.

One form of the present technology comprises a self-optimising respiratory therapy system that is configured to converge on an "optimal" respiratory therapy program for a given patient, i.e. a respiratory therapy program that most effectively treats that patient's particular condition. A practical approximation to such an "optimal" therapy program is one that maximises the chances of a given patient becoming compliant according to predetermined compliance rules. A therapy program involves device settings, patient interface selection, and engagement that both reinforces positive behaviour and seeks to address any residual problems. The disclosed self-optimising respiratory therapy system is a "closed-loop" system that periodically refines the patient's respiratory therapy program based on their device usage history and any changes in their profile so as to "learn" the patient's optimal therapy program with minimal manual involvement.

According to one aspect of the present technology, there is provided a method of treating with, or monitoring use of, a respiratory pressure therapy device for treating a respiratory disorder of a patient. The method may include analysing in a processor data relating to respiratory therapy delivered to the patient via a respiratory pressure therapy device to generate data representing a compliance prediction about the progress of the respiratory therapy. The method may include selecting an action with the processor to improve the respiratory therapy based on the data representing the compliance prediction. The method may include taking or prompting the selected action with the processor to improve the respiratory therapy.

According to a second aspect of the present technology, there is provided a system for treating a respiratory disorder in a patient. The system may include a server configured to communicate with a respiratory pressure therapy device, the respiratory pressure therapy device may be configured to deliver respiratory therapy to the patient. The server may include a processor configured to analyse data relating to the respiratory therapy delivered to the patient via the respiratory pressure therapy device to generate data representing a compliance prediction about the progress of the respiratory therapy. The processor of the server may be further configured to select an action to improve the respiratory therapy based on the data representing the compliance prediction. The processor of the server may be further configured to take or to prompt the selected action to improve the respiratory therapy.

According to a third aspect of the present technology, there is provided a server. The server may include a processor. The processor may be configured to analyse data relating to respiratory therapy delivered to a patient via a respiratory pressure therapy device to generate data in the processor representing a compliance prediction about the progress of the respiratory therapy. The processor may be configured to select an action to improve the respiratory therapy based on the data representing the compliance prediction. The processor may be configured to take or prompt the selected action to improve the respiratory therapy.

Other aspects of the present technology may be considered in reference to the particular examples and claims recited herein.

Systems and methods described herein provide technological solutions to help improve patient therapy and/or compliance with therapy such as when using a therapy device (e.g., a respiratory pressure therapy device). Moreover, in some cases it may assist with the management of such patients by a management entity (e.g., clinicians/caregivers, etc.). Moreover, the methods and systems provide improvements in the functioning of processors such as for, or control of, therapy devices and/or management or monitoring computer systems (e.g., servers).

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

7 BRIEF DESCRIPTION OF THE DRAWINGS

The present technology is illustrated by way of example, and not by way of limitation, in the figures of the accompanying drawings, in which like reference numerals refer to similar elements including:

7.1 Therapy Systems

FIG. 1 shows a therapy system including a patient 1000 wearing a patient interface 3000, in the form of a nasal pillows, receiving a supply of air at positive pressure from a RPT device 4000. Air from the RPT device 4000 is humidified in a humidifier 5000, and passes along an air circuit 4170 to the patient 1000. A bed partner 1100 is also shown.

7.2 Respiratory System and Facial Anatomy

FIG. 2 shows an overview of a human respiratory system including the nasal and oral cavities, the larynx, vocal folds, oesophagus, trachea, bronchus, lung, alveolar sacs, heart and diaphragm.

7.3 Patient Interface

FIG. 3 shows a patient interface in the form of a nasal mask in accordance with one form of the present technology.

7.4 RPT Device

7.5 Humidifier

Figure 5:
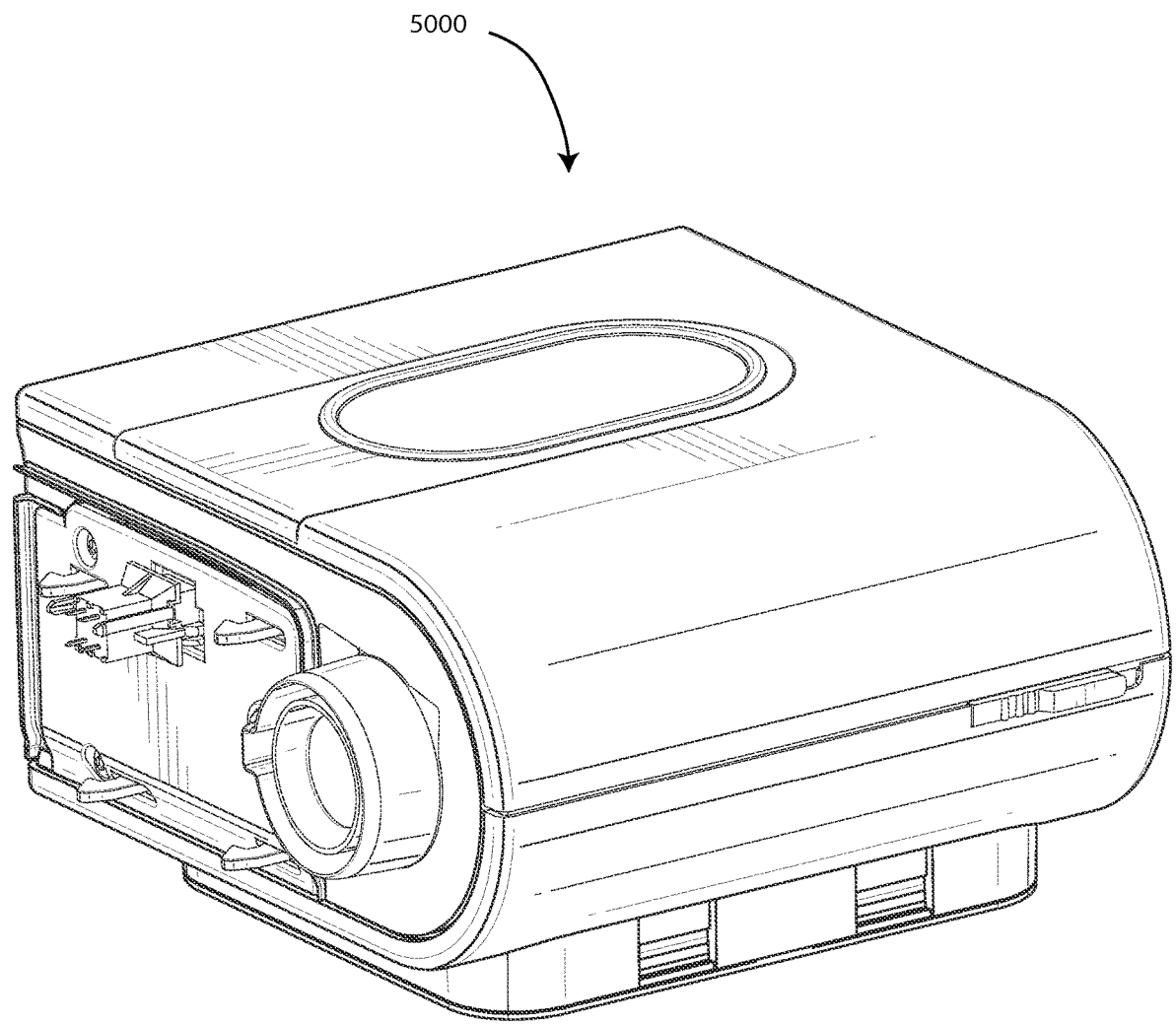

FIG. 5 shows an isometric view of a humidifier in accordance with one aspect of the present technology.

7.6 Breathing Waveforms

Figure 6A:
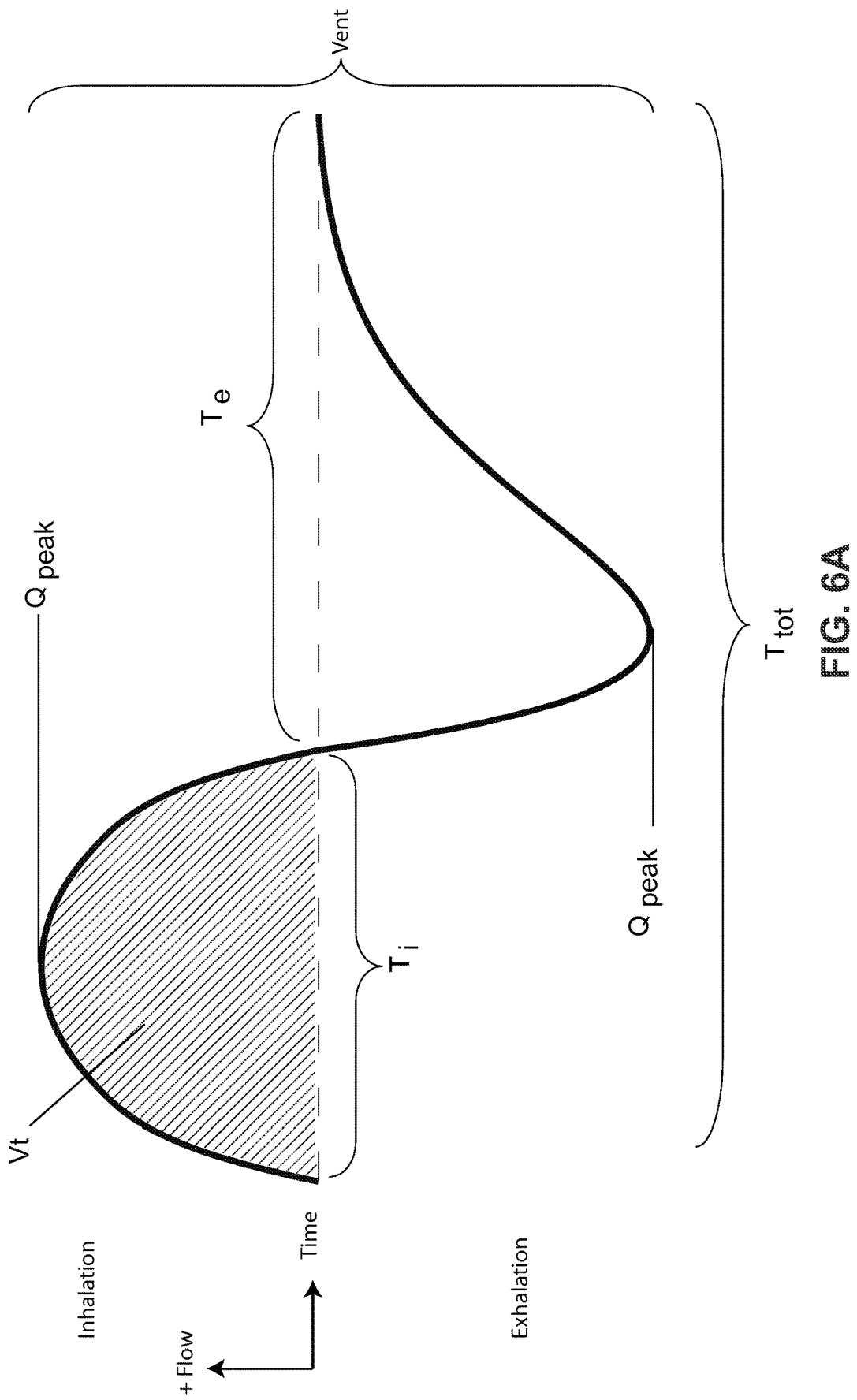

FIG. 6A shows a model typical breath waveform of a person while sleeping.

Figure 6B:
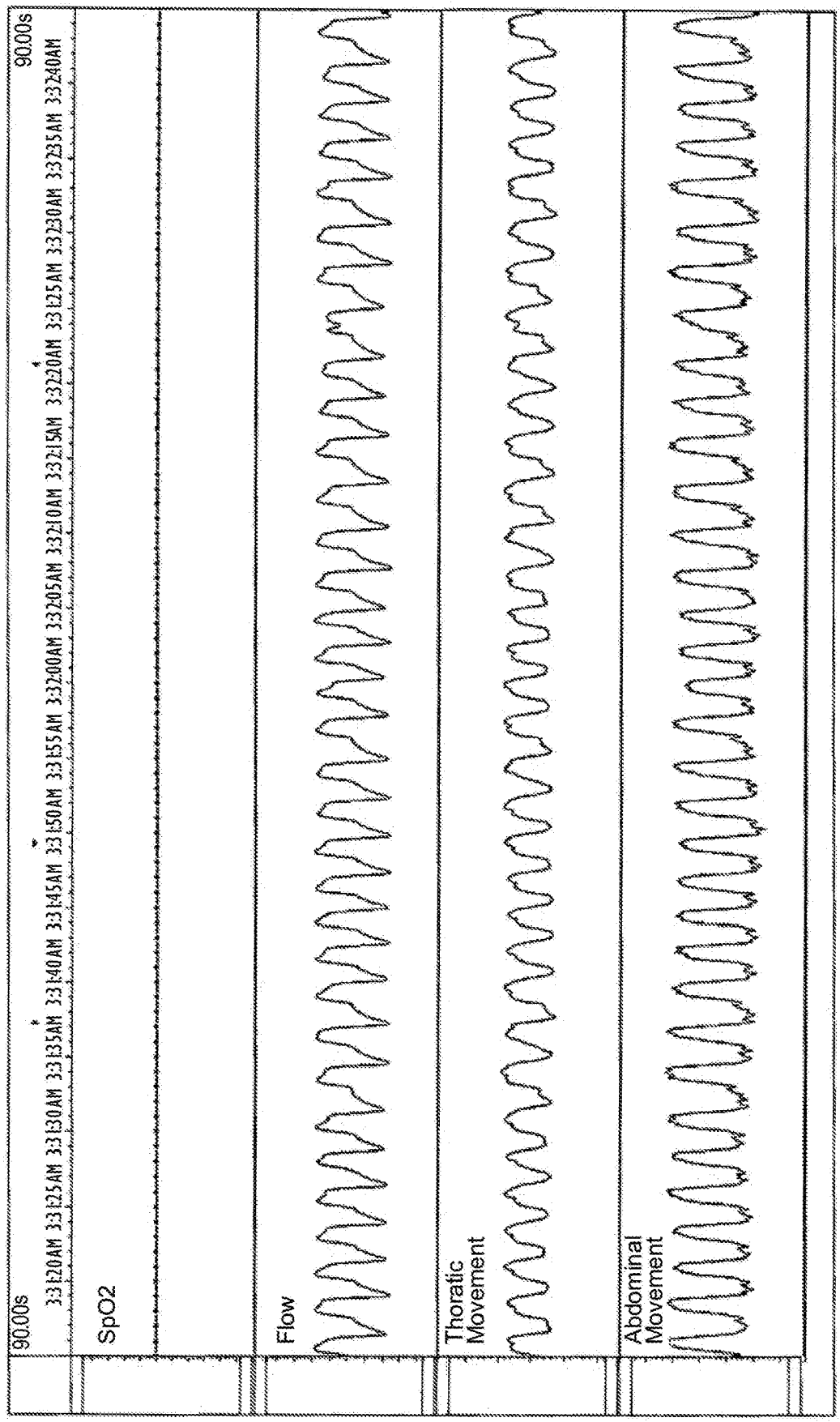

FIG. 6B shows a patient during Non-REM sleep breathing normally over a period of about ninety seconds.

Figure 6C:
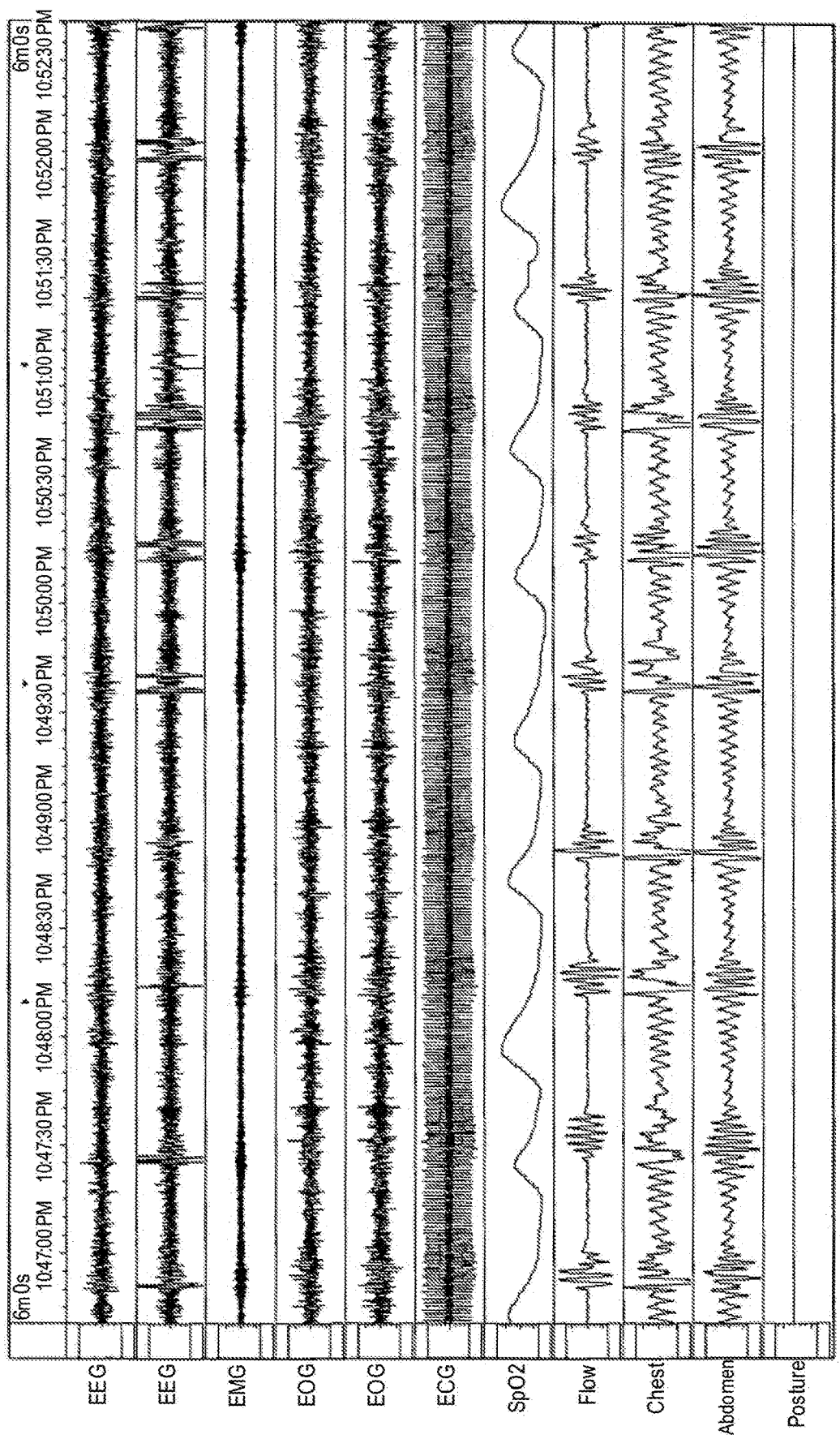

FIG. 6C shows polysomnography of a patient before treatment.

Figure 6D:
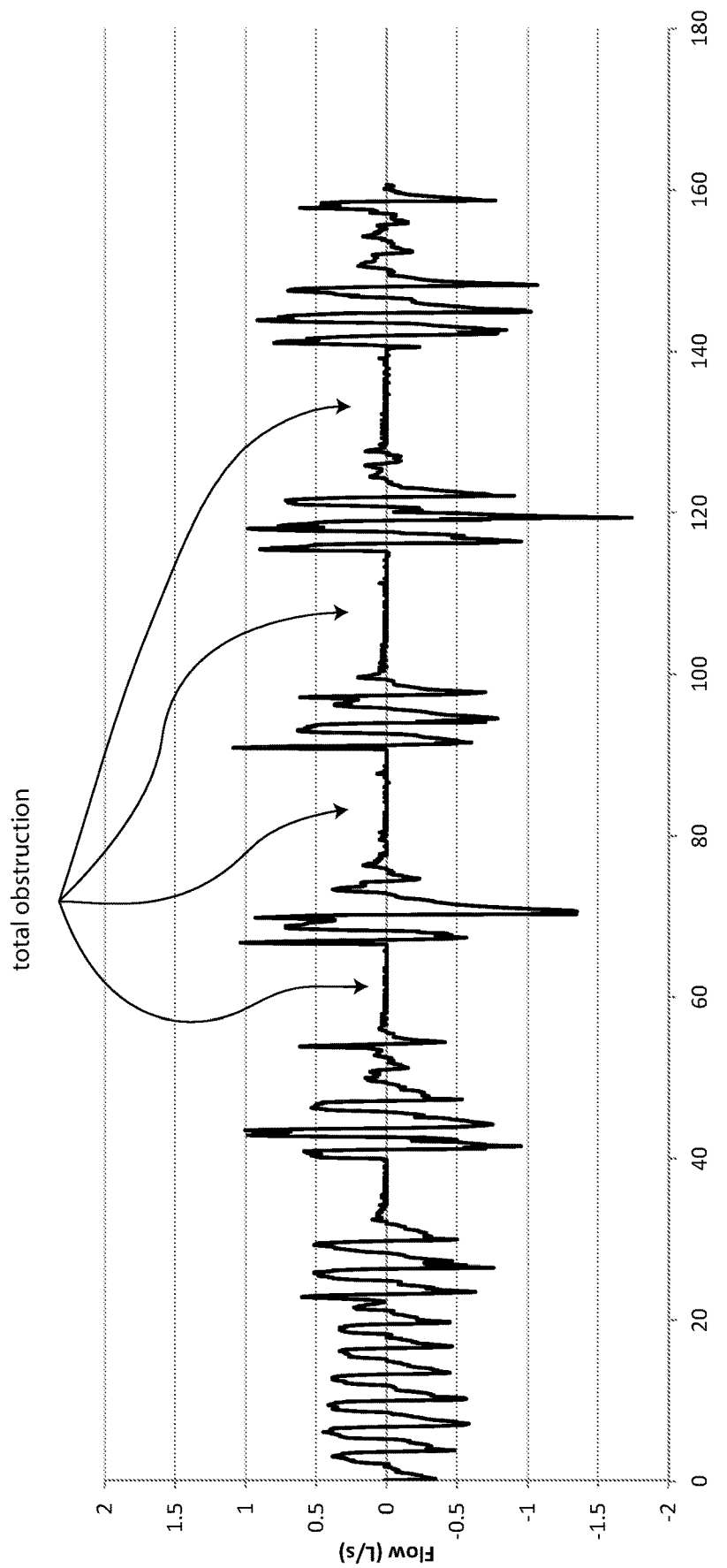

FIG. 6D shows patient flow data where the patient is experiencing a series of total obstructive apneas.

7.7 Self-Optimising Respiratory Therapy System

Figure 7A:
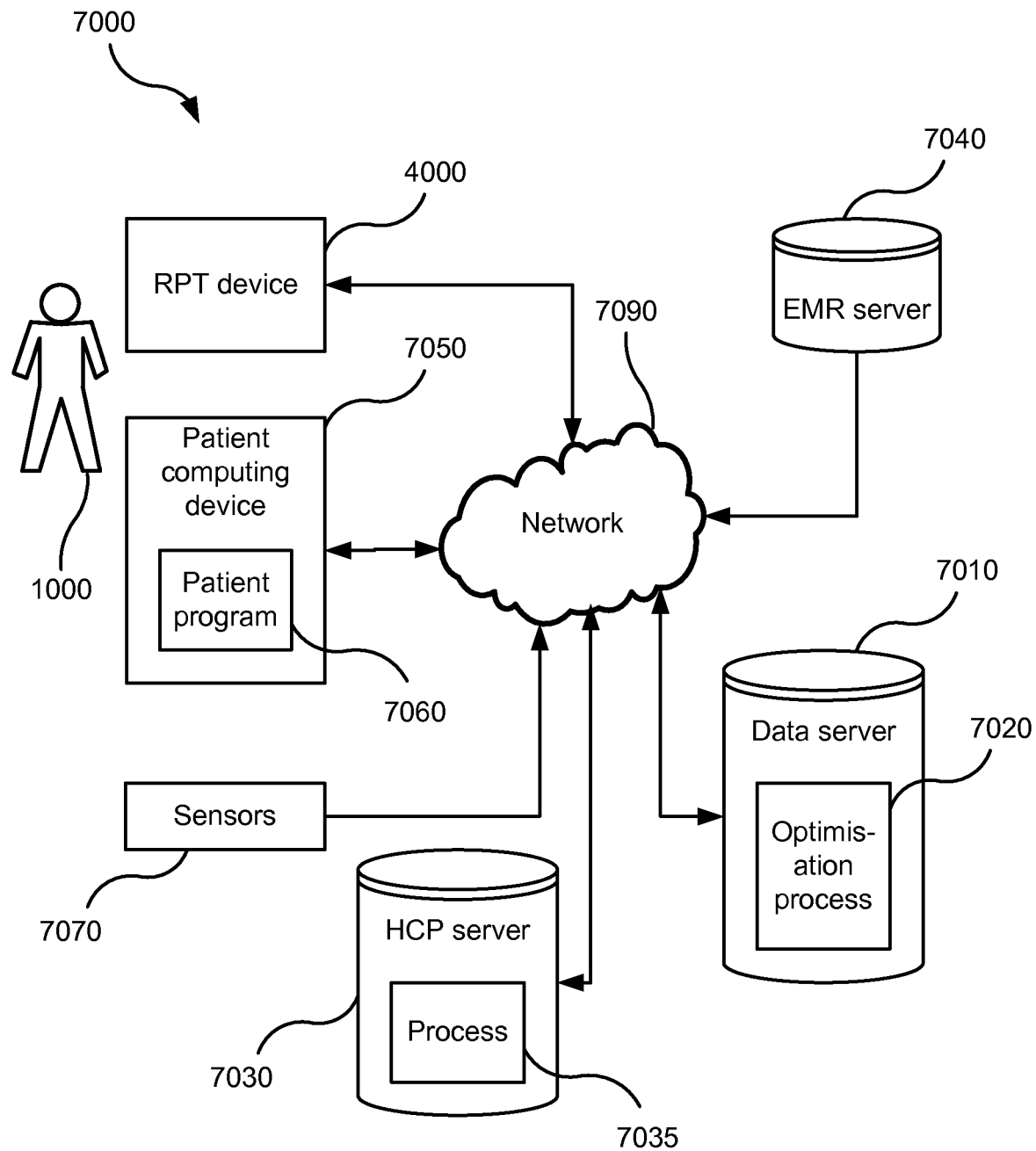

FIG. 7A is a block diagram illustrating one implementation of a self-optimising respiratory therapy system according to the present technology.

Figure 7B:
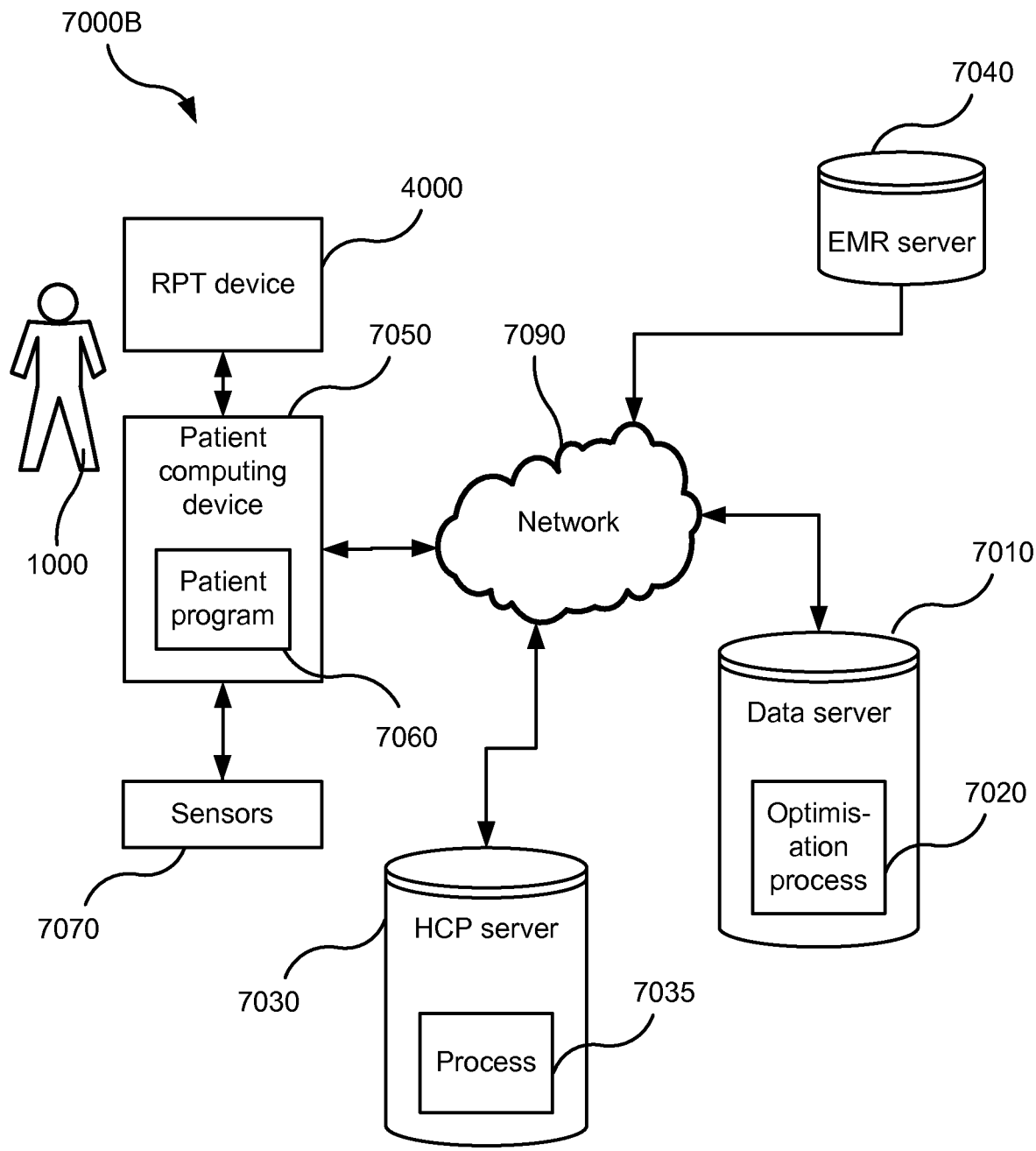

FIG. 7B is a block diagram illustrating an alternative implementation of a self-optimising respiratory therapy system according to the present technology.

Figure 8:
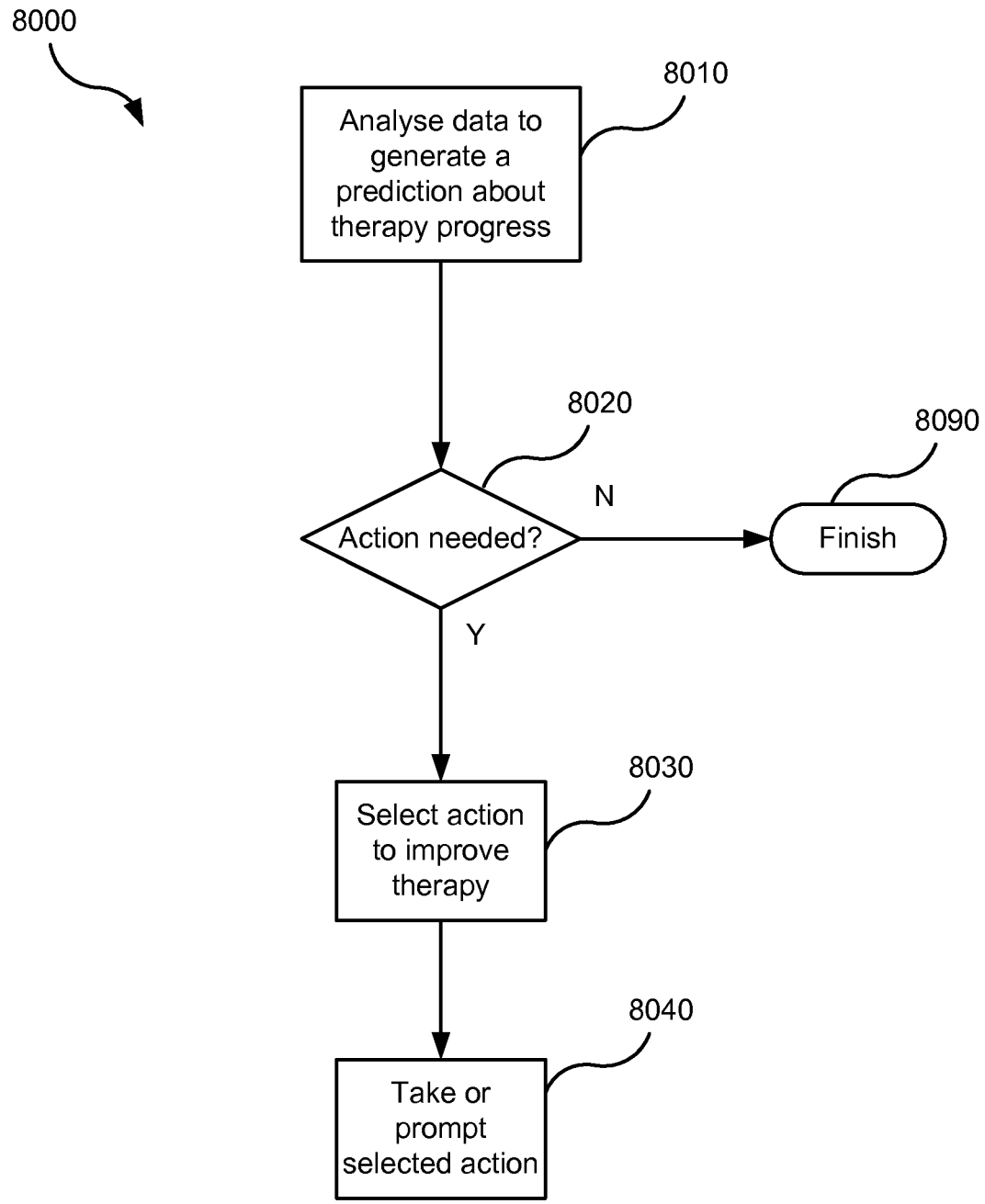

FIG. 8 is a flow diagram illustrating a method implementing the optimisation process of the self-optimising respiratory therapy system of FIG. 7A or FIG. 7B, in one form of the present technology.

Figure 9:
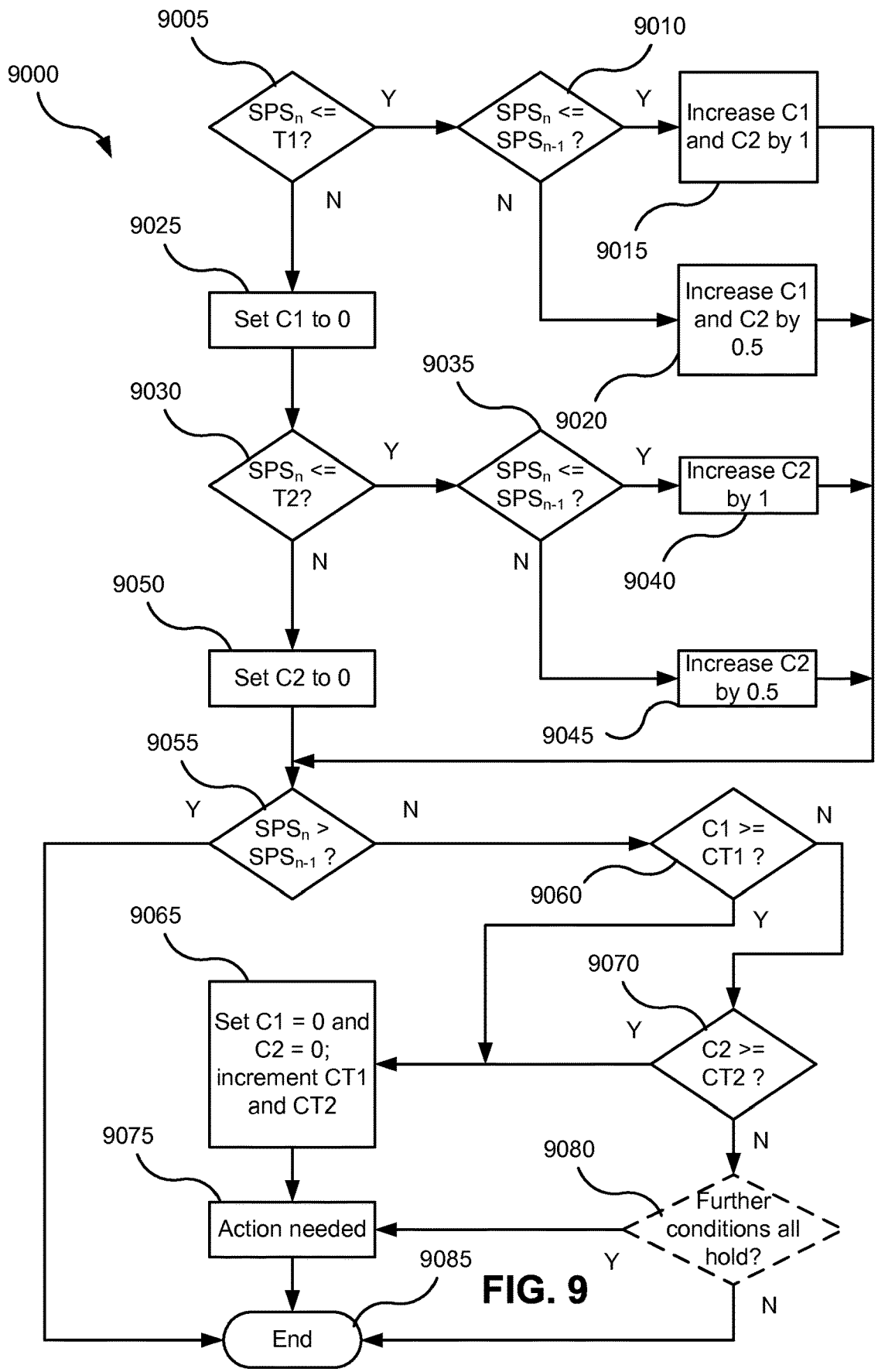

FIG. 9 is a flow chart illustrating a method that may be used to implement the determination step of the method of FIG. 8 in one form of the present technology.

8 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

8.1 Therapy

In one form, the present technology comprises a method for treating a respiratory disorder comprising the step of applying positive pressure to the entrance of the airways of a patient 1000.

In certain embodiments of the present technology, a supply of air at positive pressure is provided to the nasal passages of the patient via one or both nares.

In certain embodiments of the present technology, mouth breathing is limited, restricted or prevented.

8.2 Therapy Systems

In one form, the present technology comprises a device for treating a respiratory disorder. The device may comprise a RPT device 4000 for supplying pressurised air to the patient 1000 via an air circuit 4170 to a patient interface 3000.

8.3 Patient Interface

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

8.4 RPT Device

A preferred RPT device 4000 in accordance with one aspect of the present technology comprises mechanical and pneumatic components 4100 and electrical components 4200. The RPT device preferably has an external housing 4010, preferably formed in two parts, an upper portion 4012 and a lower portion 4014. Furthermore, the external housing 4010 may include one or more panel(s) 4015. Preferably the RPT device 4000 comprises a chassis 4016 that supports one or more internal components of the RPT device 4000. The RPT device 4000 may include a handle 4018.

The pneumatic path of the RPT device 4000 preferably comprises one or more air path items, e.g. an inlet air filter 4112, an inlet muffler 4122, a pressure generator 4140 capable of supplying air at positive pressure (preferably a blower 4142), an outlet muffler 4124 and one or more transducers 4270, such as pressure sensors 4272 and flow sensors 4274

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 preferably has an electrical power supply 4210, one or more input devices 4220, a central controller 4230, a therapy device controller 4240, a pressure generator 4140, one or more protection circuits 4250, memory 4260, transducers 4270, data communication interface 4280 and one or more output devices 4290. Electrical components 4200 may be mounted on a single Printed Circuit Board Assembly (PCBA) 4202. In an alternative form, the RPT device 4000 may include more than one PCBA 4202.

8.4.1 RPT Device Mechanical & Pneumatic Components

An RPT device may comprise one or more of the following components in an integral unit. In an alternative form, one or more of the following components may be located as respective separate units.

8.4.1.1 Air Filter(s)

A RPT device 4000 in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

8.4.1.2 Muffler(s)

An RPT device 4000 in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

8.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers housed in a volute. The blower may be preferably capable of delivering a supply of air, for example at a rate of up to about 120 litres/minute, at a positive pressure in a range from about 4 cmH$_2$O to about 20 cmH$_2$O, or in other forms up to about 30 cmH$_2$O. The blower may be as described in any one of the following patents or patent applications the contents of which are incorporated herein in their entirety: U.S. Pat. No. 7,866,944; U.S. Pat. No. 8,638,014; U.S. Pat. No. 8,636,479; and PCT patent application publication number WO 2013/020167.

The pressure generator 4140 is under the control of the therapy device controller 4240.

In other forms, a pressure generator 4140 may be a piston-driven pump, a pressure regulator connected to a high pressure source (e.g. compressed air reservoir), or a bellows.

8.4.1.4 Transducer(s)

Transducers may be internal of the RPT device 4000, or external of the RPT device 4000. External transducers may be located for example on or form part of the air circuit, e.g. the patient interface. External transducers may be in the form of non-contact sensors such as a Doppler radar movement sensor that transmit or transfer data to the RPT device 4000.

In one form of the present technology, one or more transducers 4270 are located upstream and/or downstream of the pressure generator 4140. The one or more transducers 4270 may be constructed and arranged to measure properties such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

8.4.1.4.1 Flow Transducer

A flow transducer 4274 in accordance with the present technology may be based on a differential pressure transducer, for example, an SDP600 Series differential pressure transducer from SENSIRION.

In one form, a signal representing a flow rate such as a total flow rate Qt from the flow transducer 4274 is received by the central controller 4230.

8.4.1.4.2 Pressure Transducer

A pressure transducer 4272 in accordance with the present technology is located in fluid communication with the pneumatic path. An example of a suitable pressure transducer is a sensor from the HONEYWELL ASDX series. An alternative suitable pressure transducer is a sensor from the NPA Series from GENERAL ELECTRIC.

In one form, a signal from the pressure transducer 4272 is received by the central controller 4230.

8.4.1.4.3 Motor Speed Transducer

In one form of the present technology a motor speed transducer 4276 is used to determine a rotational velocity of the motor 4144 and/or the blower 4142. A motor speed signal from the motor speed transducer 4276 is preferably provided to the therapy device controller 4240. The motor speed transducer 4276 may, for example, be a speed sensor, such as a Hall effect sensor.

8.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

8.4.1.6 Air Circuit

An air circuit 4170 in accordance with an aspect of the present technology is a conduit or a tube constructed and arranged in use to allow a flow of air to travel between two components such as the pneumatic block 4020 and the patient interface 3000.

In particular, the air circuit 4170 may be in fluid connection with the outlet of the pneumatic block and the patient interface. The air circuit may be referred to as an air delivery tube. In some cases there may be separate limbs of the circuit for inhalation and exhalation. In other cases a single limb is used.

8.4.1.7 Oxygen Delivery

In one form of the present technology, supplemental oxygen 4180 is delivered to one or more points in the pneumatic path, such as upstream of the pneumatic block 4020, to the air circuit 4170 and/or to the patient interface 3000.

8.4.2 RPT Device Electrical Components

8.4.2.1 Power Supply

A power supply 4210 may be located internal or external of the external housing 4010 of the RPT device 4000.

In one form of the present technology power supply 4210 provides electrical power to the RPT device 4000 only. In another form of the present technology, power supply 4210 provides electrical power to both RPT device 4000 and humidifier 5000.

8.4.2.2 Input Devices

In one form of the present technology, a RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

8.4.2.3 Central Controller

In one form of the present technology, the central controller 4230 is one or a plurality of processors suitable to control a RPT device 4000.

Suitable processors may include an x86 INTEL processor, a processor based on ARM Cortex-M processor from ARM Holdings such as an STM32 series microcontroller from ST MICROELECTRONIC. In certain alternative forms of the present technology, a 32-bit RISC CPU, such as an STR9 series microcontroller from ST MICROELECTRONICS or a 16-bit RISC CPU such as a processor from the MSP430 family of microcontrollers, manufactured by TEXAS INSTRUMENTS may also be suitable.

In one form of the present technology, the central controller 4230 is a dedicated electronic circuit.

In one form, the central controller 4230 is an application-specific integrated circuit. In another form, the central controller 4230 comprises discrete electronic components.

The central controller 4230 may be configured to receive input signal(s) from one or more transducers 4270, and one or more input devices 4220.

The central controller 4230 may be configured to provide output signal(s) to one or more of an output device 4290, a therapy device controller 4240, a data communication interface 4280 and humidifier 5000.

In some forms of the present technology, the central controller 4230 is configured to implement one or more therapy algorithms expressed as computer programs stored in a non-transitory computer readable storage medium, such as memory 4260. In some forms of the present technology, the central controller 4230 may be integrated with a RPT device 4000. However, in some forms of the present technology, some methodologies may be performed by a remotely located device. For example, the remotely located device may determine control settings for the RPT device 4000 or detect respiratory related events by analysis of stored data such as from any of the sensors described herein.

8.4.2.4 Clock

Preferably RPT device 4000 includes a clock 4232 that is connected to the central controller 4230.

8.4.2.5 Therapy Device Controller

Therapy device controller 4240 in accordance with one aspect of the present technology receives as input a prescribed treatment pressure Pt, and controls the pressure generator 4140 to deliver a flow of air whose mask pressure Pm at the patient interface 3000 is equal to the prescribed treatment pressure Pt.

In one form of the present technology, the prescribed treatment pressure Pt is manually entered to the RPT device 4000 via the input devices 4220. In other forms, the prescribed treatment pressure Pt is hard-coded to the RPT device 4000 at the time of configuration of the RPT device 4000.

In one form of the present technology, therapy device controller 4240 is a control module that forms part of the therapy algorithms executed by the central controller 4230.

In one form of the present technology, therapy device controller 4240 is a dedicated motor control integrated circuit. For example, in one form a MC33035 brushless DC motor controller, manufactured by ONSEMI, is used.

8.4.2.6 Protection Circuits

The one or more protection circuits 4250 in accordance with the present technology may comprise an electrical protection circuit, a temperature and/or pressure safety circuit.

8.4.2.7 Memory

In accordance with one form of the present technology the RPT device 4000 includes memory 4260, preferably non-volatile memory. In some forms, memory 4260 may include battery powered static RAM. In some forms, memory 4260 may include volatile RAM.

Preferably memory 4260 is located on the PCBA 4202. Memory 4260 may be in the form of EEPROM, or NAND flash.

Additionally or alternatively, RPT device 4000 includes a removable form of memory 4260, for example a memory card made in accordance with the Secure Digital (SD) standard.

In one form of the present technology, the memory 4260 acts as a non-transitory computer readable storage medium on which are stored computer program instructions expressing the one or more therapy algorithms.

8.4.2.8 Data Communication Systems

In one preferred form of the present technology, a data communication interface 4280 is provided, and is connected to the central controller 4230. Data communication interface 4280 is preferably connectable to remote external communication network 4282 and/or a local external communication network 4284. Preferably remote external communication network 4282 is connectable to remote external device 4286. Preferably local external communication network 4284 is connectable to local external device 4288.

In one form, data communication interface 4280 is part of the central controller 4230. In another form, data communication interface 4280 is separate from the central controller 4230, and may comprise an integrated circuit or a processor.

In one form, remote external communication network 4282 is the Internet. The data communication interface 4280 may use wired communication (e.g. via Ethernet, or optical fibre) or a wireless protocol (e.g. CDMA, GSM, LTE) to connect to the Internet.

In one form, local external communication network 4284 utilises one or more communication standards, such as Bluetooth, WiFi, NFC, Bluetooth LE or a consumer infrared protocol.

In one form, remote external device 4286 is one or more computers, for example a cluster of networked computers. In one form, remote external device 4286 may be virtual computers, rather than physical computers. In either case, such remote external device 4286 may be accessible to an appropriately authorised person such as a clinician or other health care provider.

Local external device 4288 may be a personal computer, mobile phone, tablet, or remote control.

8.4.2.9 Output Devices Including Optional Display, Alarms

An output device 4290 in accordance with the present technology may take the form of one or more of a visual, audio and haptic unit. A visual display may be a Liquid Crystal Display (LCD) or Light Emitting Diode (LED) display.

8.4.2.9.1 Display Driver

A display driver 4292 receives as an input the characters, symbols, or images intended for display on the display 4294, and converts them to commands that cause the display 4294 to display those characters, symbols, or images.

8.4.2.9.2 Display

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

8.4.3 Respiratory Therapy Algorithms

In one form of the present technology, the central controller 4230 executes one or more algorithms for the determination of one or more respiratory therapy parameters.

In one form of the present technology, the respiratory therapy parameter is an instantaneous treatment pressure Pt. In one implementation of this form, the treatment pressure Pt is given by $$Pt = AP(\Phi) + P_0 \qquad (1)$$

where:

A is a pressure support parameter,

P ($\Phi$) is a pressure-phase waveform value (in the range 0 to 1) at a current value $\Phi$ of phase of the respiratory cycle, and $P_0$ is a base pressure parameter.

Determination of treatment pressure according to equation (1) may be within minimum and maximum limits Pmin and Pmax.

Various respiratory therapy modes may be defined depending on the values of the parameters A and $P_0$. In some implementations of this form of the present technology, the pressure support A is identically zero, so the treatment pressure Pt is identically equal to the base pressure $P_0$ throughout the respiratory cycle. Such implementations are generally grouped under the heading of CPAP therapy.

The base pressure $P_0$ may be a constant value that is prescribed and/or manually entered to the RPT device 4000. This alternative is sometimes referred to as constant CPAP therapy. Alternatively, the base pressure $P_0$ may be continuously computed as a function of indices or measures of one or more of sleep disordered breathing events such as flow limitation, apnea, hypopnea, patency, and snore. This alternative is sometimes referred to as APAP therapy.

In other implementations of this form, referred to as positive pressure ventilation, the pressure support A is non-zero. In some such implementations, in which the RPT device 4000 acts as a servo-ventilator, the therapy parameter determination algorithm takes as input a current measure Vent of ventilation and a target ventilation value Vtgt and calculates a value of pressure support A to bring the current measure Vent of ventilation towards the target value Vtgt of ventilation. In such implementations, the pressure-phase waveform P (Φ) is configured so as to attain a higher value during the inspiration portion of the respiratory cycle, and a lower value during the expiration portion of the respiratory cycle.

In such implementations, the therapy parameter determination algorithm may apply a continuous control methodology to compute the pressure support A. One such continuous control methodology is Proportional-Integral (PI) control, according to which the pressure support is computed as:

$$A = G\int (\text{Vent} - \text{Vtgt}) dt \qquad (2)$$

where G is the gain of the PI control.

8.5 Humidifier

In one form of the present technology there is provided a humidifier 5000 (e.g. as shown in FIG. 5) to change the absolute humidity of air for delivery to a patient relative to ambient air. Typically, the humidifier 5000 is used to increase the absolute humidity and increase the temperature of the flow of air (relative to ambient air) before delivery to the patient's airways.

8.6 Breathing Waveforms

FIG. 6A shows a model typical breath waveform of a person while sleeping. The horizontal axis is time, and the vertical axis is respiratory flow. While the parameter values may vary, a typical breath may have the following approximate values: tidal volume, Vt, 0.5 L, inhalation time, Ti, 1.6 s, peak inspiratory flow rate, Qpeak, 0.4 L/s, exhalation time, Te, 2.4 s, peak expiratory flow rate, Qpeak, −0.5 L/s. The total duration of the breath, Ttot, is about 4 s. The person typically breathes at a rate of about 15 breaths per minute (BPM), with Ventilation, Vent, about 7.5 L/minute. A typical duty cycle, the ratio of Ti to Ttot is about 40%.

FIG. 6B shows a patient during non-REM sleep breathing normally over a period of about ninety seconds, with about 34 breaths, being treated with Automatic PAP, and the mask pressure being about 11 cmH$_2$O. The top channel shows oximetry (SpO$_2$), the scale has a range of saturation from 90 to 99% in the vertical direction. The patient maintained a saturation of about 95% throughout the period shown. The second channel shows quantitative respiratory airflow, and the scale ranges from −1 to +1 L/s in a vertical direction, and with inspiration positive. Thoracic and abdominal movement are shown in the third and fourth channels.

FIG. 6C shows polysomnography of a patient before treatment. There are eleven signal channels from top to bottom with a 6 minute horizontal span. The top two channels are both EEG (electoencephalogram) from different scalp locations. Periodic spikes in the second EEG represent cortical arousal and related activity. The third channel down is submental EMG (electromyogram). Increasing activity around the time of arousals represents genioglossus recruitment. The fourth & fifth channels are EOG (electro-oculogram). The sixth channel is an electocardiogram. The seventh channel shows pulse oximetry (SpO$_2$) with repetitive desaturations to below 70% from about 90%. The eighth channel is respiratory airflow using nasal cannula connected to a differential pressure transducer. Repetitive apneas of 25 to 35 seconds alternate with 10 to 15 second bursts of recovery breathing coinciding with EEG arousal and increased EMG activity. The ninth channel shows movement of chest and the tenth shows movement of abdomen. The abdomen shows a crescendo of movement over the length of the apnea leading to the arousal. Both become untidy during the arousal due to gross body movement during recovery hyperpnea. The apneas are therefore obstructive, and the condition is severe. The lowest channel is posture, and in this example it does not show change.

FIG. 6D shows patient flow data where the patient is experiencing a series of total obstructive apneas. The duration of the recording is approximately 160 seconds. Flow ranges from about +1 L/s to about −1.5 L/s. Each apnea lasts approximately 10-15 s.

8.7 Self-Optimising Respiratory Therapy System

8.7.1 System Architecture

Figure 1:
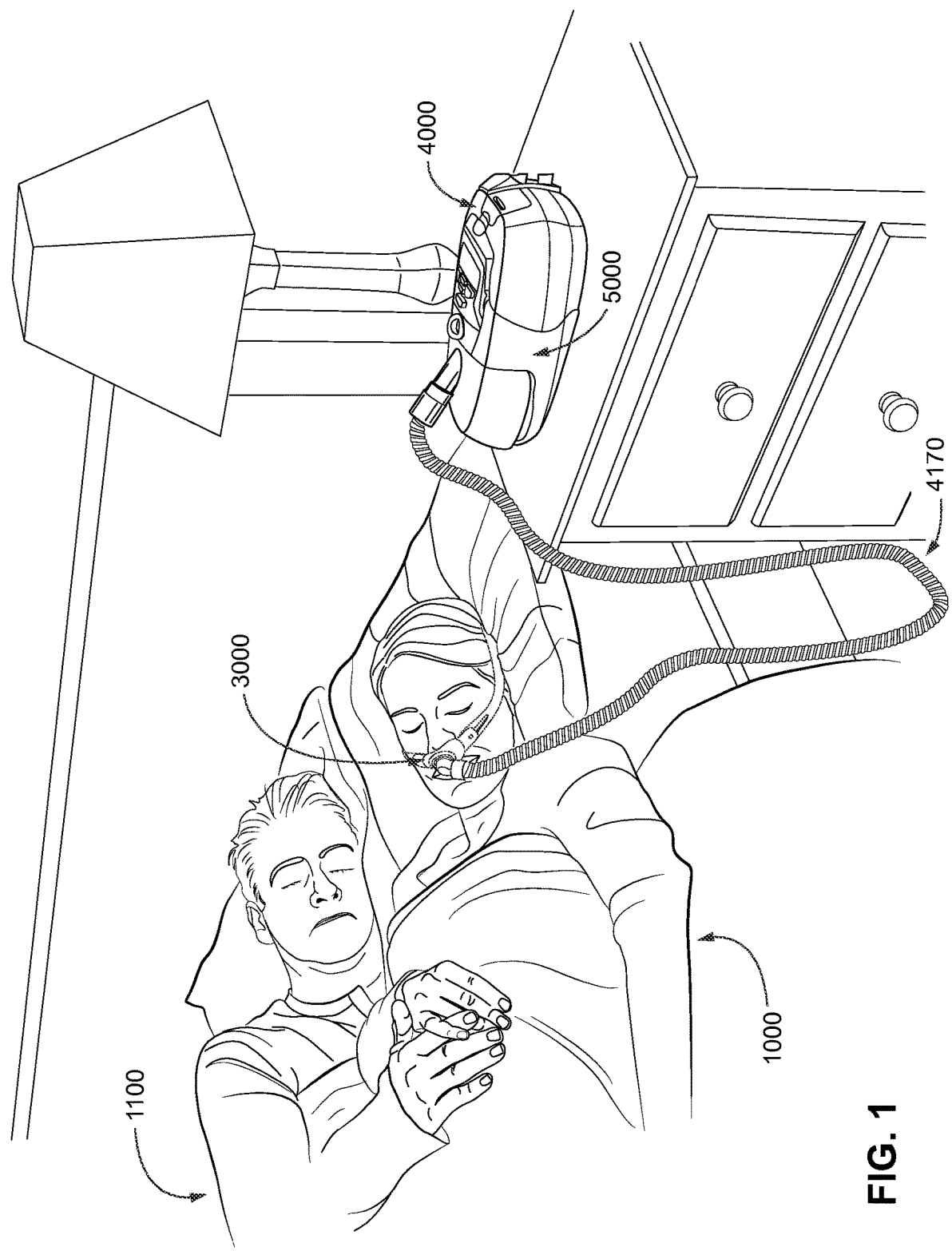
Figure 2:
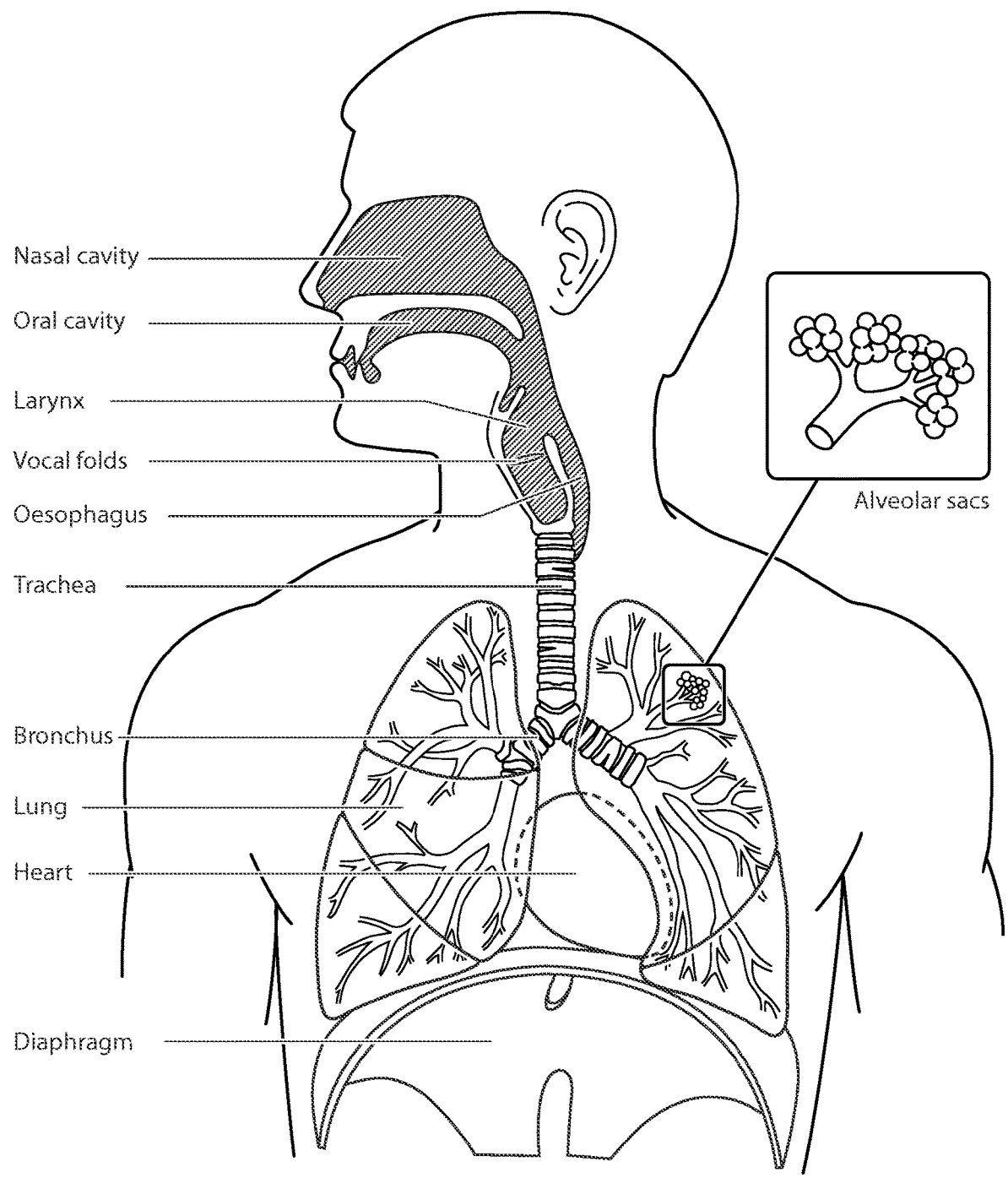
Figure 3:
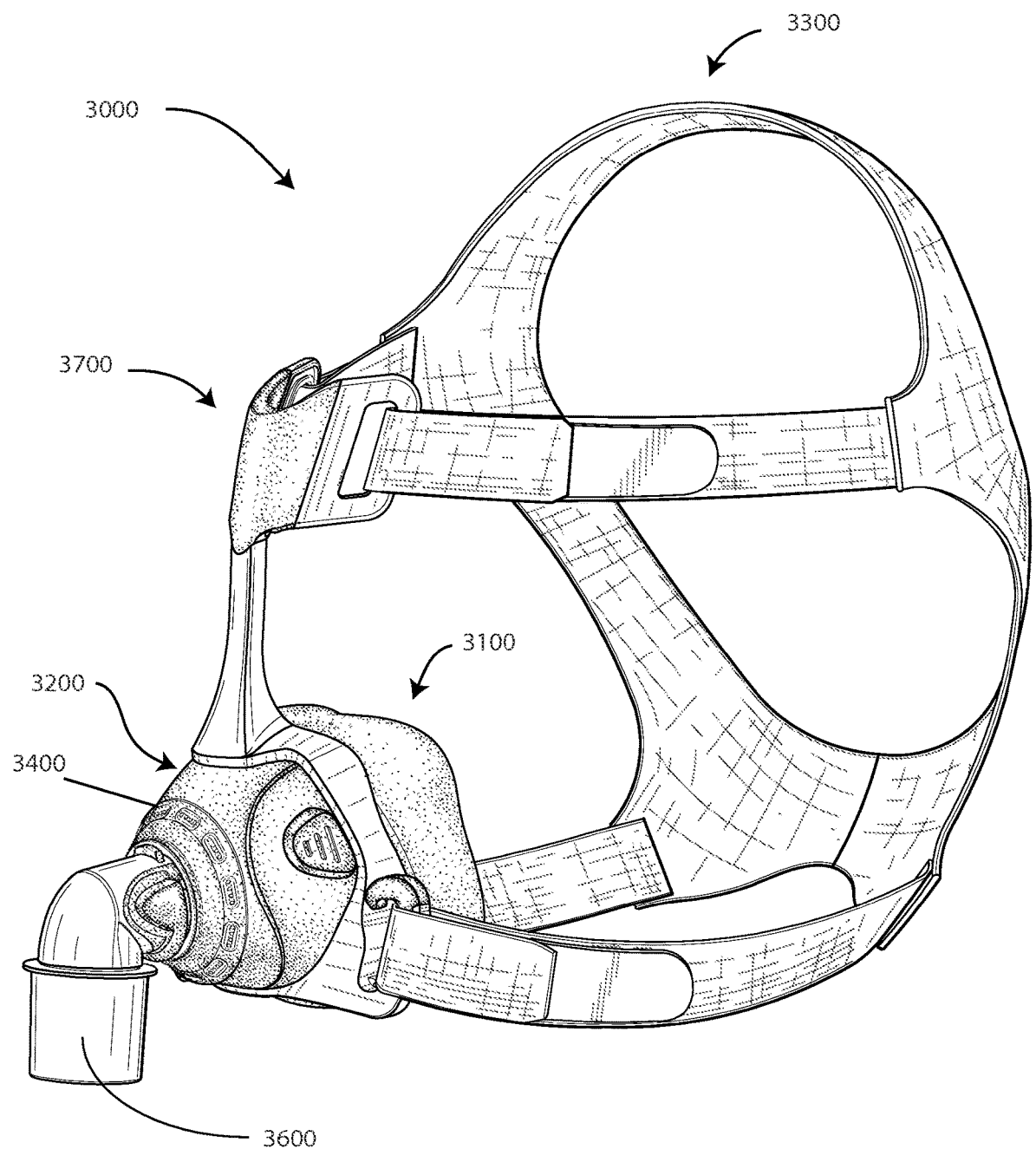
Figure 4A:
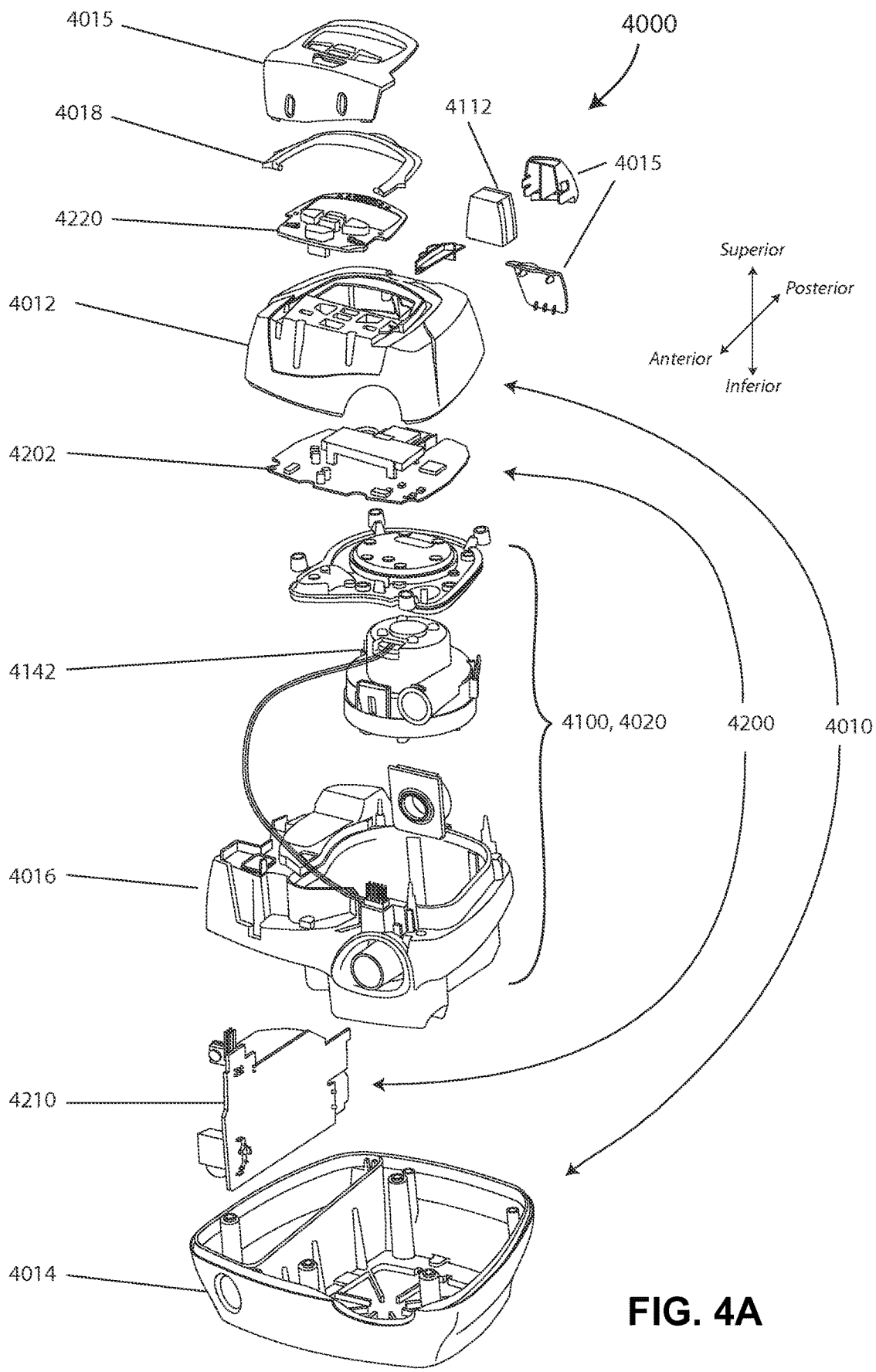
FIG. 4A shows a RPT device in accordance with one form of the present technology.
Figure 4B:
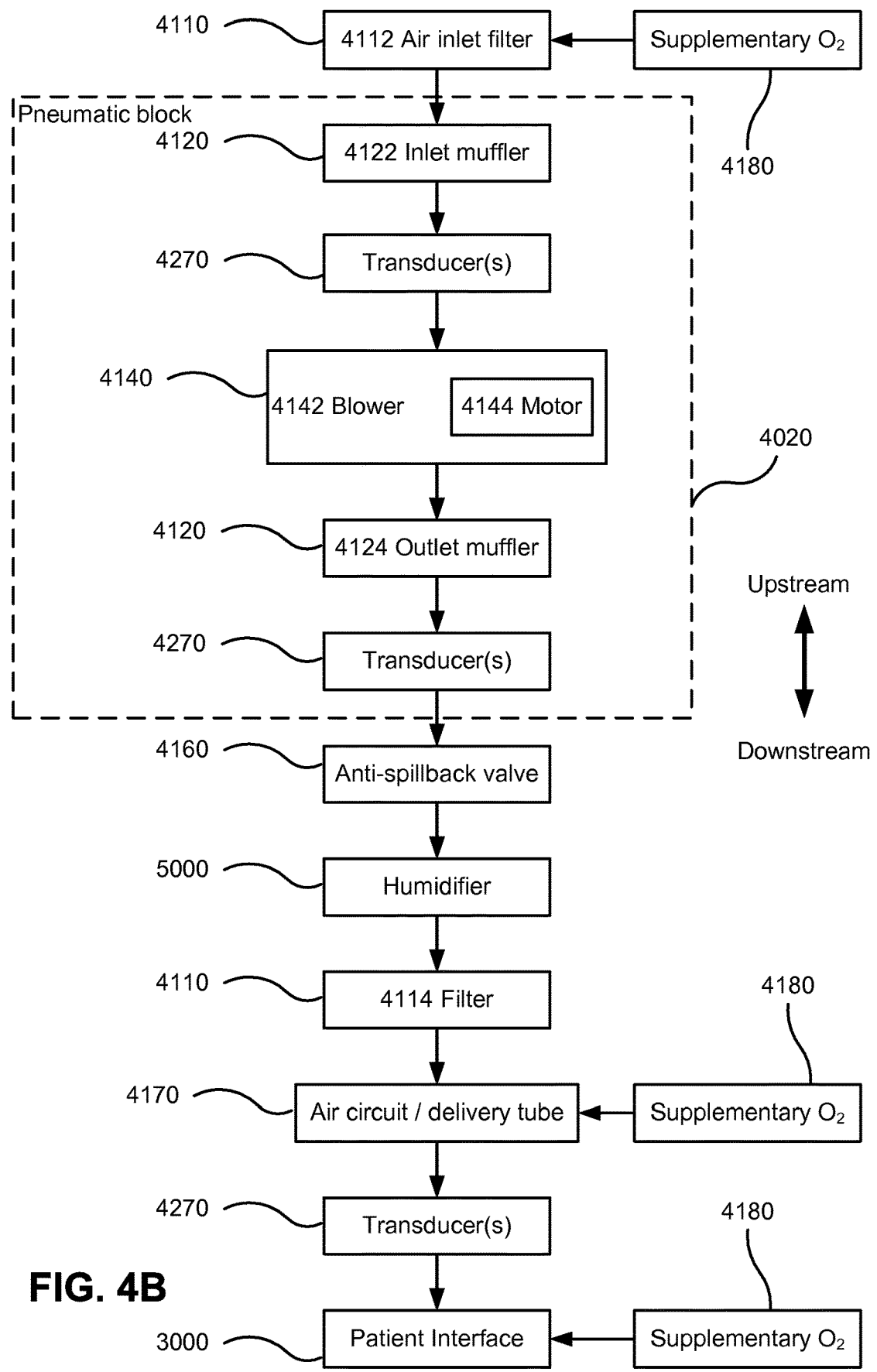
FIG. 4B shows a schematic diagram of the pneumatic path of a RPT device in accordance with one form of the present technology. The directions of upstream and downstream are indicated.
Figure 4C:
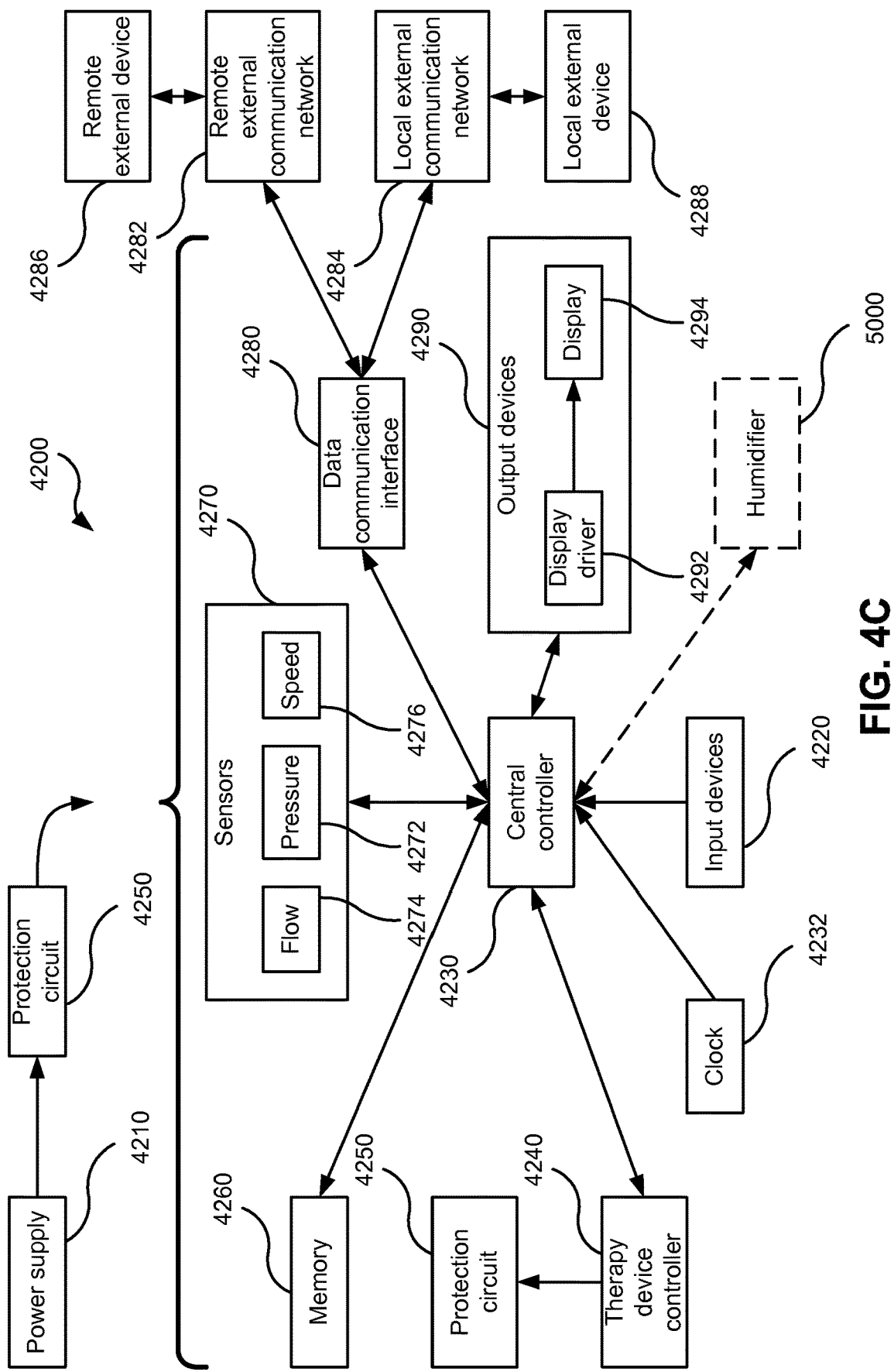
FIG. 4C shows a schematic diagram of the electrical components of a RPT device in accordance with one aspect of the present technology.

FIG. 7A contains a block diagram illustrating one implementation of a self-optimising respiratory therapy (SORT) system 7000 according to the present technology. The SORT system 7000 comprises an RPT device 4000 configured to provide respiratory therapy to a patient 1000, a data server 7010, a health or home care provider (HCP) server 7030, an electronic medical records (EMR) server 7040, a patient computing device 7050, and one or more physiological sensors 7070. The patient computing device 7050 and physiological sensors 7070 are co-located with the patient 1000 and the RPT device 4000. In the implementation 7000 shown in FIG. 7A, these entities are all connected to, and configured to communicate with each other over, a wide area network 7090, such as the Internet. The connections to the wide area network 7090 may be wired or wireless. The wide area network 7090 may be identified with the remote external communication network 4282 of FIG. 4C. The patient computing device 7050 may be a personal computer, mobile phone, tablet computer, or other device. The patient computing device 7050 is configured to intermediate between the patient 1000 and the remotely located entities of the SORT system 7000 over the wide area network 7090. In the implementation of FIG. 7A, this intermediation is accomplished by a software application program 7060 that runs on the patient computing device 7050. In one example, the patient program 7060 may be a dedicated application referred to as a "patient app". In another example, the patient program 7060 is a web browser that interacts with a web site.

In an alternative implementation of the SORT system 7000B, illustrated in FIG. 7B, the sensors 7070 and the RPT device 4000 communicate with the patient computing device 7050 via a local wired or wireless network (not shown) based on a protocol such as Bluetooth. In the alternative implementation of the SORT system 7000B, the local network may be identified with the local external communication network 4284 of FIG. 4C, and the patient computing device 7050 may be identified with the local external device 4288 of FIG. 4C. In this alternative implementation, the patient computing device 7050, via the patient program 7060, intermediates between the sensors 7070 and the RPT device 4000 and the remotely located entities of the SORT system 7000B over the wide area network 7090.

The SORT system 7000 may contain other RPT devices (not shown) associated with respective patients who also have respective associated computing devices and associated HCP servers (possibly shared with other patients). All the patients in the SORT system 7000 or 7000B may be managed by the data server 7010.

The RPT device 4000 is configured to store therapy data from each therapy session in the memory 4260. Therapy data for a session comprises the settings of the RPT device 4000, and therapy variable data representing one or more variables of the respiratory therapy throughout the therapy session.

The device settings data may include:
Base treatment pressure $P_0$
Maximum and minimum treatment pressure limits Pmax and Pmin
Target ventilation Vtgt
Pressure support A
The therapy variables may include:
Respiratory flow rate Qr
Mask pressure Pm
Leak flow Ql
Tidal volume Vt
Measure of ventilation Vent
Breathing rate The RPT device 4000 is configured to transmit the therapy data to the data server 7010. The data server 7010 may receive the therapy data from the RPT device 4000 according to a "pull" model whereby the RPT device 4000 transmits the therapy data in response to a query from the data server 7010. Alternatively, the data server 7010 may receive the therapy data according to a "push" model whereby the RPT device 4000 transmits the therapy data to the data server 7010 as soon as it is available after a therapy session.

Therapy data received from the RPT device 4000 is stored and indexed by the data server 7010 so as to be uniquely associated with the RPT device 4000 and therefore distinguishable from therapy data from any other RPT device(s) participating in the SORT system 7000. In this regard, although only one RPT device is illustrated in FIGS. 7A and 7B for ease of explanation, as mentioned above, the SORT systems 7000 and 7000B may contain multiple RPT devices.

The data server 7010 is configured to calculate summary data for each session from the therapy data received from the RPT device 4000. Summary data variables for a session comprise summary statistics derived by conventional scoring means from the therapy variable data that forms part of the therapy data. Summary data may comprise one or more of the following summary variables:

Usage time, i.e. duration of the respiratory therapy session (sometimes referred to as usage data)
Apnea-hypopnea index (AHI) for the session
Average leak flow rate for the session
Average mask pressure for the session
Other statistical summaries of the therapy variables, e.g. $95^{th}$ percentile, median, histogram Summary variables may comprise multi-session statistics, such as mean, median, and variance of AHI since the start of therapy.

In an alternative implementation, the RPT device 4000 calculates the summary variables from the therapy data stored by the RPT device 4000 at the end of each session. The RPT device 4000 then transmits the summary variables to the data server 7010 according to the "push" or "pull" model described above.

In a further alternative implementation, the memory 4260 in which the RPT device 4000 stores the therapy data or the summary data for each therapy session is in removable form, such as an SD memory card. The removable memory 4260 is removed from the RPT device 4000 and inserted into a card reader in communication with the data server 7010. The therapy data or the summary data is then copied from the removable memory 4260 to the memory of the data server 7010.

In still a further alternative implementation, suitable for the alternative implementation of the SORT system 7000B, the RPT device 4000 is configured to transmit the therapy data to the patient computing device 7050 via a wireless protocol such as Bluetooth, which receives the data as part of the patient program 7060. The patient computing device 7050 then transmits the therapy data to the data server 7010, possibly along with summary data. The data server 7010 may receive the data from the patient computing device 7050 according to a "pull" model whereby the patient computing device 7050 transmits the therapy data in response to a query from the data server 7010. Alternatively, the data server 7010 may receive the therapy data according to a "push" model whereby the patient computing device 7050 transmits the therapy data to the data server 7010 as soon as it is available after a therapy session.

In some implementations, the data server 7010 may carry out some post-processing of the summary data. One example of such post-processing is to determine whether the most recent session is a "compliant session". Some compliance rules specify the required RPT device usage over a compliance period, such as 30 days, in terms of a minimum duration of device usage per session, such as four hours, for some minimum number of days, e.g. 21, within the compliance period.

A session is deemed compliant if its duration exceeds the minimum duration. The summary data post-processing may determine whether the most recent session is a compliant session by comparing the usage time with the minimum duration from the compliance rule. The results of such post-processing are referred to as "compliance data". One example of multi-session compliance data is a count of compliant sessions since the start of therapy.

The HCP server 7030 is associated with the health/home care provider (which may be an individual health care professional or an organisation) that is responsible for the patient's respiratory therapy. An HCP may also be referred to as a DME or HME (domestic/home medical equipment provider). The HCP server 7030 hosts a process 7035 that is described in more detail below. One function of the HCP server process 7035 is to transmit data relating to the patient 1000 to the data server 7010, possibly in response to a query received from the data server 7010.

The EMR server 7040 contains electronic medical records (EMRs), both specific to the patient 1000 and generic to a larger population of patients with similar respiratory disorders to the patient 1000. An EMR, sometimes referred to as an electronic health record (EHR), typically contains a medical history of a patient including previous conditions, treatments, co-morbidities, and current status. The EMR server 7040 may be located, for example, at a hospital where the patient 1000 has previously received treatment. The EMR server 7040 is configured to transmit EMR data to the data server 7010, possibly in response to a query received from the data server 7010.

The data server 7010 may also be configured to receive data from the patient computing device 7050. Such may include data entered by the patient 1000 to the patient program 7060, behavioural data about how the patient is interacting with the patient program 7060, or therapy/summary data in the alternative implementation described above. In the implementation of the SORT system 7000B, in which the RPT device 4000 communicates with the patient computing device 7050, the behavioural data may also include data indicating how the patient is interacting with the RPT device 4000.

The data server 7010 may also be configured to receive physiological data from the one or more physiological sensors 7070. The sensors 7070 may include Doppler radar motion sensors, accelerometers, thermometers, scales, or photoplethysmographs, each of which is configured to provide physiological data (biomotion, physical activity, temperature, weight, and oxygen saturation respectively) of the patient 1000.

The data server 7010 is also configured to transmit electronic messages to the patient computing device 7050. Such messages are used to implement the engagements that form part of the patient's respiratory therapy program. In other words, the engagement with the patient takes place through the patient computing device 7050. The messages may be in various modes of engagement such as emails, SMS messages, automated voice messages, or notifications within the patient program 7060. Some such messages may prompt the patient 1000 for a response via the same mode. For example, an SMS message may prompt the patient 1000 to acknowledge that they have read and understood the message. Such responses are transmitted from the patient computing device 7050 to the data server 7010, where they are stored as "engagement data". If no response was received when prompted for, the engagement data may represent that fact.

In some implementations, the data server 7010 is configured to communicate with the HCP server 7030 to trigger notifications or action recommendations to an agent of the HCP such as a nurse, or to support reporting of various kinds. Examples of recommended actions include phone calls and personal visits to the patient 1000 by a nurse or technician. Such actions are also used to implement certain forms of engagement as part of the patient's respiratory therapy program. Details of actions carried out are stored by the data server 7010 as part of the engagement data.

In some implementations, the data server 7010 is configured to transmit control commands to the RPT device 4000. A control command may be an instruction to adjust a setting of the RPT device 4000.

The data server 7010 hosts an optimisation process 7020, described below, that implements the "self-optimising" part of the SORT system 7000. In general, the optimisation process 7020 analyses data from the RPT device 4000, the patient computing device 7050, the sensors 7070, the HCP server 7030, and the EMR server 7040, to generate a prediction about the progress of the therapy being delivered to the patient 1000. The optimisation process 7020 then selects an action intended to improve the patient's respiratory therapy based on the prediction, and takes or prompts another entity in the SORT system 7000 to take the selected action.

As mentioned above, the HCP server 7030 hosts an HCP server process 7035 that communicates with the optimisation process 7020 and the patient program 7060 as described in more detail below.

The EMR server 7040, the HCP server 7030, and the data server 7010 may all be implemented on distinct computing devices at separate locations, or any sub-combination of two or more of those entities may be co-implemented on the same computing device.

8.7.2 System Operation

FIG. 8 contains a block diagram illustrating a method 8000 carried out by the data server 7010 in the SORT system 7000 of FIG. 7A or 7000B of FIG. 7B in one form of the present technology. In one form of the present technology, the optimisation process 7020 comprises repeated execution of the method 8000. The repetition may be according to a schedule, or may be event-driven, such as upon receipt of therapy data or summary data for a new therapy session.

The method 8000 starts at step 8010, at which the data server 7010 analyses the data available to it in order to generate a prediction about the progress of the therapy being delivered to the patient 1000. The data available to the data server 7010 and analysed in the step 8010 may comprise one or more of the following: profile data, behavioural data, therapy data, physiological data, summary data, compliance data, EMR data, engagement data, and HCP data. Engagement data is not available until a therapy program has been initiated.

The profile data may include demographic data such as patient age, sex, marital status, weight, occupation, address, education level, and nationality, and the primary care physician who prescribed the therapy. The profile data may also include details of the prescribed respiratory therapy, such as type and model of the RPT device 4000, the initial settings of the RPT device 4000, and type, model, and size of patient interface 3000 to be used. In one implementation of the SORT system 7000, the patient 1000 enters the profile data to the patient program 7060 when enrolling in the SORT system 7000, and the patient computing device 7050 transmits the profile data to the data server 7010. In another implementation, an operator of the HCP server 7030 enters the profile data manually to the HCP server 7030 via the HCP server process 7035 when enrolling the patient 1000 in the SORT system 7000, and the HCP server process 7035 transmits the profile data to the data server 7010.

The profile data may also include answers to a behavioural-based screener or questionnaire. As with the profile data itself, in one implementation, the patient 1000 may enter the screener answers to the patient program 7060 when enrolling in the SORT system 7000 in response to questions presented by the patient program 7060, and the patient program 7060 transmits the screener answers to the data server 7010. In another implementation, an operator of the HCP server 7030 enters the screener answers manually to the HCP server 7030 via the HCP server process 7035 when administering the screener as part of enrolling the patient 1000 in the SORT system 7000, and the HCP server process 7035 transmits the screener answers to the data server 7010.

The screener may include one or more of the following questions, among others:

Have you ever dieted? If so, how would you rate your success in achieving your weight loss goals?

How likely are you to use your device for x days out of the next y days for z hours or more per night (where x, y, and z depend on the compliance rule)?

How self-disciplined are you, on a scale of one to ten?

The result of step 8010 is a prediction about the progress of the therapy being delivered to the patient 1000.

In one implementation of step 8010, the data server 7010 applies a compliance model to the data to predict the compliance of the patient 1000 with the predetermined compliance rule. Such a compliance prediction is represented by a Success Predictor Score (SPS) indicating the probability that the patient will be compliant with the predetermined compliance rule. In one example, the SPS is a numerical value, such as a percentage or fraction representing the probability that the patient will be compliant.

Alternatively, the SPS may be one of a set of labels indicating the likelihood of future compliance, such as: 'very unlikely', 'unlikely', 'moderately likely', 'likely', and 'very likely'. An example of a compliance model is described below.

In another implementation of step 8010, suitable for patients with chronic respiratory disease such as COPD, the data server 7010 applies an event model to the data to estimate the probability of the patient 1000 experiencing a clinical event related to their chronic condition, such as a COPD exacerbation.

In yet another implementation of step 8010, the data server 7010 applies an event model to the data to estimate the probability of the patient 1000 having, or developing, a co-morbid condition with their respiratory disorder. In one example, a combined analysis of profile data and questionnaire responses could indicate a predisposition toward diabetes.

Step 8010 may applies different models to generate different kinds of prediction at different executions of the method 8000. For example, during one execution of the method 8000, step 8010 may apply a compliance model to generate a compliance prediction, and during a subsequent execution, step 8010 may apply an event model to generate a clinical event prediction.

Following step 8010, at step 8020 the method 8000 determines whether any action is needed to improve the patient's respiratory therapy, based on the prediction computed at step 8010. If no action is needed ("N"), at step 8090 the method 8000 concludes. Otherwise ("Y"), the method 8000 proceeds to step 8030.

At step 8030, the data server 7010 uses the data representing the prediction computed at step 8010, and possibly other available data, to select an action to improve the patient's respiratory therapy. Finally, at step 8040, the data server 7010 takes or prompts another entity in the SORT system 7000 to take the selected action. The method 8000 then concludes.

In one implementation of step 8030, suitable for the first execution of the method 8000, the determination at step 8020 returns "Y" for all patients 1000. The action selected by the data server 7010 at step 8030 is then to choose values for the parameters of the therapy program. The parameters of a respiratory therapy program may include:

Device settings
Patient interface model, type, and size
Engagement rule set

The engagement rule set of a therapy program is a set of one or more rules specifying the details of the engagement with the patient 1000. Engagement rules are described in more detail below.

In one implementation of step 8040, suitable for the first execution of the method 8000, the data server 7010 initiates the therapy program selected for the patient 1000 using the parameter values chosen at step 8030.

Initiating a therapy program includes initiating the engagement portion of the therapy program. For example, if the engagement rules of the selected therapy program specify an engagement at the start of therapy, the data server 7010 sends a welcome message to the patient 1000 via the patient computing device 7050. The welcome message may contain motivational content, and/or details of the selected therapy program, such as settings for the RPT device 4000. If the welcome message prompts the patient 1000 for a response, the data server 7010 stores any response from the patient 1000 in the engagement data.

The engagement rules of the selected therapy program may specify a manual mode of engagement, such as a phone call or a personal visit. In such a case, the data server 7010 at step 8040 prompts the HCP server process 7035 to trigger notifications or action recommendations to an agent of the HCP.

In implementations of the SORT system 7000 in which the settings of the RPT device 4000 are able to be adjusted remotely, initiation of the selected therapy program may involve sending a control command to the RPT device 4000 to set its settings in accordance with the device settings parameters of the selected therapy program.

Once a therapy program is initiated, the data server 7010 continues to perform or prompt the engagements according to the engagement rule set in the therapy program.

In one implementation of step 8020, suitable for second and subsequent executions of the method 8000, the data server 7010 determines whether the computed SPS value from step 8010 is less than a threshold (e.g. 25%), indicating a high risk that the patient will not be compliant with the predetermined compliance rule.

In a more sophisticated implementation of step 8020, also suitable for second and subsequent executions of the method 8000, the data server 7010 applies a number of heuristics to the SPS computed at step 8010 to determine whether an action to improve the patient's therapy is needed.

FIG. 9 is a flow chart illustrating a method 9000 that may be performed by the data server 210 to implement the determination of step 8020. The method 9000 takes into account not only the computed value $SPS_n$ of the SPS at the most recent therapy session n, but also the value $SPS_{n-1}$ of the SPS computed at the previous session (n–1), in order to determine whether action is needed. The method 9000 determines that action is needed when a patient remains at a "high" or "medium" level of non-compliance risk for a minimum number of sessions. Each time an action is deemed to be needed at step 8020, the minimum number of sessions is increased. This design ensures that step 8020 responds quickly to a "high" or "medium" level of non-compliance risk while limiting the number of times an action is taken at step 8040.

In the method 9000, which is suitable for a numerically-valued SPS, two counts, C1 and C2, are maintained depending on comparison of $SPS_n$ with respective thresholds T1 and T2 (T1 being less than T2), representing "high" and "medium" levels of non-compliance risk respectively. Each count is incremented if $SPS_n$ falls below the corresponding threshold, and doubly incremented if the SPS has not increased since the previous session. Each count is set to zero otherwise. In an alternative implementation of step 8020, suitable for a label-valued SPS, the counts C1 and C2 are incremented if $SPS_n$ is "very unlikely" or "unlikely" respectively.

If the SPS has not increased since the previous session, the counts C1 and C2 are compared with respective count thresholds CT1 and CT2. If either count exceeds its corresponding count threshold, action is deemed to be needed, both counts are reset to zero, and the count thresholds are incremented. Otherwise, some further conditions that may also result in an action may optionally be checked. The incrementing of the count thresholds once an action has been deemed needed means that it becomes harder for actions to be deemed to be needed thereafter.

The method 9000 starts at step 9005, which determines whether $SPS_n$ is less than or equal to the first threshold T1. In one implementation, the first threshold T1 is set to 0.2 (20%). If so ("Y"), step 9010 checks whether $SPS_n$ is less than or equal to $SPS_{n-1}$, indicating that the SPS is not increasing. If so ("Y"), step 9015 increases both counts C1 and C2 by one. Otherwise ("N"), step 9020 increases both counts C1 and C2 by 0.5. In either case, the method 9000 then proceeds to step 9055.

If step 9005 found that $SPS_n$ is greater than the first threshold T1 ("N"), step 9025 sets the first count C1 to zero. Step 9030 then determines whether $SPS_n$ is less than or equal to the second threshold T2. In one implementation, the second threshold T2 is set to 0.4 (40%). If so ("Y"), step 9035 checks whether $SPS_n$ is less than or equal to $SPS_{n-1}$, indicating that the SPS is not increasing. If so ("Y"), step 9040 increases the second count C2 by one. Otherwise ("N"), step 9045 increases the second count C2 by 0.5. In either case, the method 9000 then proceeds to step 9055. If step 9030 found that $SPS_n$ is greater than the second threshold T2 ("N"), step 9050 sets the second count C2 to zero.

The method 9000 proceeds to step 9055, which checks whether $SPS_n$ is greater than $SPS_{n-1}$. If so ("Y"), the method 9000 concludes at step 9085. Otherwise ("N"), step 9060 checks whether the first count C1 is greater than or equal to the first count threshold CT1. If so ("Y"), step 9065 sets both counts C1 and C2 to zero, and increments both count thresholds CT1 and CT2 by one. Step 9075 then determines that action is needed, and the method 9000 concludes at step 9085.

If step 9060 determined that the first count C1 is not greater than or equal to the first count threshold CT1 ("N"), step 9070 checks whether the second count C2 is greater than or equal to the second count threshold CT2. If so ("Y"), the method proceeds to step 9065 described above. Otherwise ("N"), the method 9000 may conclude at step 9085. Alternatively, in an optional step 9080, the method 9000 checks whether all of a set of further conditions hold. If so ("Y"), the method proceeds to step 9065 described above. Otherwise ("N"), the method 9000 concludes at step 9085.

In one example of step 9080, the "further conditions" are as follows:
  n (session number for the patient) is greater than or equal to 15.
  $SPS_n$ is less than 0.5 (50%).
  $SPS_{n-1}$ is greater than 0.5 (50%).
  Action has not previously been deemed needed.

These "further conditions" detect patients who have been doing well but whose risk of non-compliance worsens significantly late in the compliance period.

In one implementation of step 8030, suitable for second and subsequent executions of the method 8000, the action selected by the data server 7010 is to adjust the therapy program based on the prediction computed at step 8010.

The adjustment to the therapy program selected at second and subsequent executions of step 8030 may be a change to the settings of the RPT device 4000. In implementations of the SORT system 7000 in which the settings of the RPT device 4000 are able to be adjusted remotely, at step 8040 the data server 7010 sends a control command to the RPT device 4000 to change its settings in accordance with the selected adjustment. In implementations of the SORT system 7000 in which the settings of the RPT device 4000 are not able to be adjusted remotely, the data server 7010 sends a message to the patient 1000 via the patient computing device 7050 to prompt the patient 1000 to adjust the settings of the RPT device 4000. In another such implementation, the data server 7010 sends a message to the HCP server process 7035 to prompt a technician or health care professional to be dispatched to the patient 1000 to adjust the settings of the RPT device 4000.

The adjustment to the therapy program selected at second and subsequent executions of step 8030 may be a change to the recommended patient interface. In one such implementation, at step 8040 the data server 7010 may transmit a message to the patient 1000 via the patient computing device 7050 to recommend the selected change. In another such implementation, the data server 7010 sends a message to the HCP server process 7035 to prompt a technician or health care professional to contact the patient 1000 to recommend the selected change.

The adjustment to the therapy program selected at subsequent executions of step 8030 may be a change to the engagement rules of the therapy program. In this case, at step 8040 the data server 7010 performs or prompts the engagements according to the changed engagement rules.

In another implementation of step 8030, suitable for second and subsequent executions of the method 8000, the action selected by the data server 7010 may be to "intervene" with the patient. An "intervention" is a general-purpose manual engagement with the patient, such as a phone call or personal visit, that is extraneous to the engagement rules in the therapy program.

In one implementation of step 8020, suitable for second and subsequent executions of the method 8000, the data server 7010 determines whether a statistic positing an intervention obtained from the compliance model is greater than a threshold. In one example, the statistic is the probability of the patient becoming compliant after an intervention, that is, the SPS re-computed under the assumption that an intervention has already taken place (the SPS after intervention). Another example of a statistic, which indicates the benefit of an intervention, is the difference between the SPS after intervention and the SPS prior to intervention (i.e. the SPS value computed at step 8010). In yet another example, which indicates the benefit/cost ratio of an intervention, the statistic is the difference between the SPS after intervention and the SPS prior to intervention, divided by the product of the SPS prior to intervention and the cost of an intervention.

In implementations using such statistics at step 8020, step 8030 simply selects an intervention.

In the implementation of step 8010 in which the data server 7010 estimates the probability of the patient 1000 experiencing a clinical event, the data server 7010 determines at step 8020 whether the estimated probability is greater than a threshold (e.g. 50%). The action selected at step 8030 may be to notify the HCP of the probable event. In this implementation, the data server 7010 at step 8040 issues an alert to the HCP server process 7035 to notify an agent of the HCP of the probable event.

In the implementation of step 8010 in which the data server 7010 estimates the probability of the patient 1000 having or developing a co-morbid condition, the data server 7010 determines at step 8020 whether the estimated probability is greater than a threshold (e.g. 50%). The action selected at step 8030 may be to notify the HCP of the probable co-morbidity. In this implementation, the data server 7010 at step 8040 issues an alert to the HCP server process 7035 to notify an agent of the HCP of the probable co-morbidity.

By repeatedly executing the method 8000, the optimisation process 7020 is configured to converge on the "optimal" respiratory therapy program for the patient 1000.

In one implementation of the method 8000, the "optimal" therapy program is the therapy program that maximises the SPS for the patient 1000. As noted above, such an "optimal" program is a practical approximation to the most effective therapy program for the patient 1000. In other implementations, the "optimal" therapy program is the therapy program that minimises the patient's AHI, maximises usage or compliance, or minimises leak.

8.7.2.1 Compliance Model

In one implementation of the optimisation process 7020 described above, step 8010 of the method 8000 applies a compliance model to compute the SPS. One implementation of a compliance model is a linear predictive model, which computes the SPS as a weighted sum of its N input feature values $f_1, \ldots, f_N$ (representing the available input data), plus a constant C:

$$SPS = C + \sum_{n=1}^{N} c_n f_n \tag{3}$$

The $c_n$ are the weighting coefficients for the respective feature values $f_n$. The SPS computed according to equation (3) may be mapped to the range [0, 1] by means of a function such as the sigmoid or the inverse tangent.

In other implementations of the step 8010, the compliance model may be a neural network, decision tree ensemble, support vector machine, Bayesian network, or gradient boosting machine. Such structures can be configured to implement either linear or non-linear predictive models.

The parameters of the compliance model, such as (in the linear predictive model) the coefficients $c_n$ and the constant C, are obtained from training carried out using historical input data according to conventional predictor training methods. In some implementations, the compliance model parameters used by the optimisation process 7020 are altered between executions of the method 8000, for example to increase or decrease the weighting of a certain feature value as therapy proceeds, according to a predetermined schedule. For example, during the first five days of therapy, one summary variable may be the most important feature, while later on, another summary variable may have a higher weighting.

8.7.2.2 Engagement Rules

The purpose of the engagements is to encourage and assist the patient 1000 to commence or persevere with their respiratory therapy.

An engagement rule comprises a condition and an engagement action to be taken if the condition is met. The engagement action of an engagement rule is a specific message in a specific mode of engagement. The mode of engagement may be automatic (email, SMS message, automated voice message, or notification to the program 7060) or manual (phone call, personal visit). An engagement message contains some kind of "coaching" content, either within the message itself or as a link to an online resource, such as a video. The content of the action in the engagement rule is related to the condition in that same rule. The content can be educational (e.g. "Clean your cushion when you get up so it has time to dry, it will seal better") or motivational (e.g. "Learning CPAP is a little like learning to drive a car. It may seem hard at first but the benefits make it all worthwhile.")

Engagement rule conditions are of two basic kinds: time-based, and exception-based. A time-based condition is met when a certain time has elapsed since the initiation of the therapy program or some other initiating event. Examples of time-based conditions are one day, four days, ten days, etc. An exception-based condition is met when a therapy variable satisfies some criterion. An example of an exception-based condition is "95th percentile leak is greater than or equal to 20 L/min". An exception-based condition may also have a time element to it, e.g. "95th percentile leak is greater than or equal to 20 L/min for 10 out of 10 to 14 consecutive days." Basic conditions may be combined using Boolean operators, in which case the rule may be referred to as a "complex rule". The content of the engagement message coupled with such a condition may be "If you know you are fitting your mask correctly and are still having major problems with mask leak, check your mask size."

Time-based conditions may be tailored to the patient in a number of ways that reflect the most propitious occasions for triggering a desired action in that patient. The best time to trigger an action is when motivation is high, i.e. a "motivation wave". Motivation waves often occur at New Year or other cultural festivals, birthdays etc., the dates of which may be obtained from the profile data of the patient 1000. The SORT system 7000 may therefore, when setting up the engagement rule set of the therapy program at the first execution of step 8030, take into account the patient profile data when setting the timings of the time-based conditions. A motivation wave may be inferred from an increased level of physical activity, which can be detected by a wearable activity sensor (which may be one of the physiological sensors 7070). The SORT system 7000 may therefore, when adjusting the timings of the time-based conditions of the engagement rule set of the therapy program at second and subsequent executions of step 8030, take into account the physical activity data from an accelerometer 7070.

An engagement rule set may be characterised by its overall level of "aggressiveness". A more aggressive engagement rule set contains more and earlier time-based conditions and/or easier thresholds for exception-based conditions than a less aggressive engagement rule set. One example of an adjustment that may be selected at step 8030 is a change to the aggressiveness of the engagement rule set. For example, if the determination at step 8020 indicates that the patient's therapy program is in need of adjustment, the adjustment selected at step 8030 might be to increase the aggressiveness of the engagement rule set to provide more and earlier time-based conditions, and/or easier thresholds for the exception-based conditions.

Another example of an adjustment that may be selected at step 8030 is a change to the engagement action of an engagement rule. For example, the adjustment may change the mode of the engagement action, e.g. from automatic to manual. In another example, the adjustment may alter the content of the engagement action. In one such implementation, all engagement messages are stored in a catalogue in association with various rule conditions. Step 8030 selects one of the messages in the catalogue that is associated with the rule condition that has been met. Over time, based on the responses by the patient 1000 to the selected engagement messages that form part of the engagement data for the patient 1000, the SORT system 7000 "learns" which is the most effective engagement message in the catalogue for a given rule condition for that patient 1000.

Studies have shown that involvement and encouragement from a partner or a caregiver of a patient can be important in getting and keeping the patient compliant. Therefore, in some implementations, an engagement action may be a message to the partner 1100 or a caregiver of the patient 1000. Some examples of partner/caregiver engagement messages and conditions are:

At the initiation of therapy: An email/SMS message "The support you give can make all the difference".

After one day: A link to a video entitled "How treatment can help you and your loved one".

If leak is high: a link to a video entitled "Improving your partner's mask seal and comfort".

After 7 days: A link to a video entitled "Noises, lights, and beeps on your partner's CPAP device".

8.8 Glossary

For the purposes of the present technology disclosure, in certain forms of the present technology, one or more of the following definitions may apply. In other forms of the present technology, alternative definitions may apply.

8.8.1 General

Air: In certain forms of the present technology, air may be taken to mean atmospheric air, and in other forms of the present technology air may be taken to mean some other combination of breathable gases, e.g. atmospheric air enriched with oxygen.

Ambient: In certain forms of the present technology, the term ambient will be taken to mean (i) external of the therapy system or patient, and (ii) immediately surrounding the therapy system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g. acoustic) noise may be considered to be the background noise level in the room where a patient is located, other than for example, noise generated by a RPT device or emanating from a mask or patient interface. Ambient noise may be generated by sources outside the room.

Continuous Positive Airway Pressure (CPAP): CPAP therapy will be taken to mean the application of a supply of air to the entrance to the airways at a pressure that is continuously positive with respect to atmosphere, and preferably approximately constant through a respiratory cycle of a patient. In some forms of CPAP therapy, the pressure at the entrance to the airways, though intended to be constant throughout the respiratory cycle, will vary over the cycle due to the patient's respiratory effort, being slightly higher during exhalation, and slightly lower during inhalation.

8.8.2 Aspects of the Respiratory Cycle

Apnea: Preferably, apnea will be said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): Preferably breathing effort will be said to be the work done by a spontaneously breathing person attempting to breathe.

Expiratory portion of a breathing cycle: The period from the start of expiratory flow to the start of inspiratory flow.

Flow limitation: Preferably, flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Hypopnea: Preferably, a hypopnea will be taken to be a reduction in flow, but not a cessation of flow. In one form, a hypopnea may be said to have occurred when there is a reduction in flow below a threshold for a duration. A central hypopnea will be said to have occurred when a hypopnea is detected that is due to a reduction in breathing effort. In one form in adults, either of the following may be regarded as being hypopneas:

(i) a 30% reduction in patient breathing for at least 10 seconds plus an associated 4% desaturation; or (ii) a reduction in patient breathing (but less than 50%) for at least 10 seconds, with an associated desaturation of at least 3% or an arousal.

Hyperpnea: An increase in flow to a level higher than normal flow.

Inspiratory portion of a breathing cycle: Preferably the period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, airflow, patient airflow rate, respiratory airflow rate (Qr): These synonymous terms may be understood to refer to the RPT device's estimate of respiratory airflow rate, as opposed to "true respiratory flow rate" or "true respiratory airflow rate", which is the actual respiratory flow rate experienced by the patient, usually expressed in litres per minute.

Tidal volume (Vt): The volume of air inhaled or exhaled during normal breathing, when extra effort is not applied.

(inhalation) Time (Ti): The duration of the inspiratory portion of the respiratory flow waveform.

(exhalation) Time (Te): The duration of the expiratory portion of the respiratory flow waveform.

(total) Time (Ttot): The total duration between the start of the inspiratory portion of one respiratory flow waveform and the start of the inspiratory portion of the following respiratory flow waveform.

Typical recent ventilation: The value of ventilation around which recent values over some predetermined timescale tend to cluster, that is, a measure of the central tendency of the recent values of ventilation.

Upper airway obstruction (UAO): includes both partial and total upper airway obstruction. This may be associated with a state of flow limitation, in which the level of flow increases only slightly or may even decrease as the pressure difference across the upper airway increases (Starling resistor behaviour).

Ventilation (Vent): A measure of the total amount of gas being exchanged by the patient's respiratory system, including both inspiratory and expiratory flow, per unit time. When expressed as a volume per minute, this quantity is often referred to as "minute ventilation". Minute ventilation is sometimes given simply as a volume, understood to be the volume per minute.

8.8.3 RPT Device Parameters

Flow rate: The instantaneous volume (or mass) of air delivered per unit time. While flow rate and ventilation have the same dimensions of volume or mass per unit time, flow rate is measured over a much shorter period of time. In some cases, a reference to flow rate will be a reference to a scalar quantity, namely a quantity having magnitude only. In other cases, a reference to flow rate will be a reference to a vector quantity, namely a quantity having both magnitude and direction. Where it is referred to as a signed quantity, a flow rate may be nominally positive for the inspiratory portion of a breathing cycle of a patient, and hence negative for the expiratory portion of the breathing cycle of a patient. 'Flow rate' is sometimes shortened to simply 'flow'. Flow rate will be given the symbol Q. Total flow rate, Qt, is the flow rate of air leaving the RPT device. Vent flow rate, Qv, is the flow rate of air leaving a vent to allow washout of exhaled gases. Leak flow rate, Ql, is the flow rate of unintentional leak from a patient interface system. Respiratory flow rate, Qr, is the flow rate of air that is received into the patient's respiratory system.

Leak: Preferably, the word leak will be taken to be a flow of air to the ambient. Leak may be intentional, for example to allow for the washout of exhaled $CO_2$. Leak may be unintentional, for example, as the result of an incomplete seal between a mask and a patient's face. In one example leak may occur in a swivel elbow.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes in the patient interface.

Pressure: Force per unit area. Pressure may be measured in a range of units, including $cmH_2O$, g-f/cm$^2$, hectopascal. 1cmH$_2$O is equal to 1 g-f/cm$^2$ and is approximately 0.98 hectopascal. In this specification, unless otherwise stated, pressure is given in units of $cmH_2O$. The pressure in the patient interface is given the symbol Pm, while the treatment pressure, which represents a target value to be achieved by the mask pressure Pm at the current instant of time, is given the symbol Pt.

8.8.4 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

8.9 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

8.10 Reference Signs List patient 1000
bed partner 1100
patient interface 3000
seal-forming structure 3100
plenum chamber 3200
structure 3300
connection port 3600
RPT device 4000
external housing 4010
upper portion 4012
portion 4014
panel 4015
chassis 4016
handle 4018
pneumatic block 4020
pneumatic component 4100
air filter 4110
inlet air filter 4112
outlet air filter 4114
muffler 4120
inlet muffler 4122
outlet muffler 4124
pressure generator 4140
blower 4142
motor 4144
anti-spill back valve 4160
air circuit 4170
supplemental oxygen 4180
electrical component 4200
PCBA 4202
electrical power supply 4210
input device 4220
central controller 4230
clock 4232
therapy device controller 4240
protection circuit 4250
memory 4260
transducer 4270
pressure transducer 4272
flow transducer 4274
motor speed transducer 4276
data communication interface 4280
remote external communication network 4282
local external communication network 4284
remote external device 4286
local external device 4288
output device 4290
display driver 4292
display 4294
humidifier 5000
breathing waveforms 6000
SORT system 7000
SORT system 7000B
data server 7010
process 7020
HCP server 7030
EMR server 7040
patient computing device 7050
patient program 7060
physiological sensors 7070
network 7090
method 8000
step 8010
step 8020
step 8030
step 8040
step 8090
method 9000
step 9005
step 9010
step 9015
step 9020
step 9025
step 9030
step 9035
step 9040
step 9045
step 9050
step 9055
step 9060
step 9065
step 9070
step 9075
step 9080
step 9085

8.11 Further Examples of the Technology

The following paragraphs further illustrate examples of the present technology described herein.

Example 1. A method of treating with, or monitoring use of, a respiratory pressure therapy device for treating a respiratory disorder of a patient, the method comprising: analysing in a processor data relating to respiratory therapy delivered to the patient via the respiratory pressure therapy device to generate data in the processor representing a compliance prediction about the progress of the respiratory therapy; selecting an action with the processor to improve the respiratory therapy based on the data representing the compliance prediction; and taking or prompting the selected action with the processor to improve the respiratory therapy.

Example 2. A method according to Example 1 (or any one of the preceding Examples), wherein the respiratory therapy is in accordance with a therapy program, and the action is an adjustment to the therapy program.

Example 3. A method according to Example 2 (or any one of the preceding Examples), wherein the therapy program comprises an engagement rule set, each rule in the rule set comprising a condition and an engagement action.

Example 4. A method according to Example 3 (or any one of the preceding Examples), wherein the adjustment to the therapy program comprises adjusting aggressiveness of the engagement rule set.

Example 5. A method according to Example 3 (or any one of the preceding Examples), wherein the data relating to respiratory therapy delivered to the patient comprises engagement data describing patient responses to previous engagement actions.

Example 6. A method according to any of Examples 1 to 5 (or any one of the preceding Examples), wherein the data relating to respiratory therapy delivered to the patient comprises therapy data.

Example 7. A method according to any of Examples 1 to 6 (or any one of the preceding Examples), wherein the data relating to respiratory therapy delivered to the patient comprises summary data comprising summary statistics of therapy data representing one or more variables of the respiratory therapy.

Example 8. A method according to any of Examples 1 to 7 (or any one of the preceding Examples), wherein the data relating to respiratory therapy delivered to the patient comprises compliance data indicating whether usage of the respiratory pressure therapy device by the patient is in accordance with a compliance rule.

Example 9. A method according to any of Examples 1 to 8 (or any one of the preceding Examples), wherein the data relating to respiratory therapy delivered to the patient comprises physiological data of the patient.

Example 10. A method according to any of Examples 1 to 9 (or any one of the preceding Examples), wherein the data relating to respiratory therapy delivered to the patient comprises profile data of the patient.

Example 11. A method according to Example 10 (or any one of the preceding Examples), wherein the profile data comprises answers supplied by the patient to a questionnaire.

Example 12. A method according to any of Examples 1 to 11 (or any one of the preceding Examples), wherein the data representing the compliance prediction is a score indicating a probability that the patient will be compliant with a predetermined compliance rule.

Example 13. A method according to Example 12 (or any one of the preceding Examples), wherein the analysing comprises applying a compliance model to the data to generate the score.

Example 14. A method according to any of Examples 1 to 13 (or any one of the preceding Examples), further comprising determining whether an action is needed before selecting an action.

Example 15. A method according to Example 14 (or any one of the preceding Examples), wherein the determining uses the data representing the compliance prediction.

Example 16. A method according to Example 15 (or any one of the preceding Examples), wherein the data representing the compliance prediction is a score indicating a probability that the patient will elect to be compliant with a predetermined compliance rule.

Example 17. A method according to Example 16 (or any one of the preceding Examples), wherein the determining comprises comparing the score with a threshold.

Example 18. A method according to Example 16 (or any one of the preceding Examples), wherein the determining comprises: determining whether the score has been less than or equal to a first threshold, and less than or equal to a score computed at a previous session, for a number of sessions equal to a first count threshold; and determining whether the score is not greater than the score computed at the previous session.

Example 19. A method according to Example 18 (or any one of the preceding Examples), wherein the determining further comprises determining whether the score has been less than or equal to a second threshold, and less than or equal to the score computed at a previous session, for a number of sessions equal to a second count threshold.

Example 20. A method according to Example 18 (or any one of the preceding Examples), wherein the determining further comprises determining whether the score satisfies a plurality of further conditions.

Example 21. A method according to Example 18 (or any one of the preceding Examples), wherein the determining further comprises incrementing the first count threshold once the patient has been determined to be at risk.

Example 22. A method according to Example 14 (or any one of the preceding Examples), wherein the action is an intervention, and the determining comprises comparing a statistic positing an intervention with a threshold.

Example 23. A method according to Example 22 (or any one of the preceding Examples), wherein the statistic is a probability of the patient becoming compliant with a predetermined compliance rule after the intervention.

Example 24. A method according to any of Examples 1 to 23 (or any one of the preceding Examples), further comprising analysing the data relating to respiratory therapy to generate a further prediction, wherein the further prediction is a probability of the patient experiencing a clinical event related to their respiratory disorder.

Example 25. A method according to Example 24 (or any one of the preceding Examples), wherein the analysing comprises applying an event model to the data.

Example 26. A method according to Example 24 (or any one of the preceding Examples), wherein the action comprises issuing an alert to a health care provider.

Example 27. A method according to any of Examples 1 to 23 (or any one of the preceding Examples), further comprising analysing the data relating to respiratory therapy to generate a further prediction, wherein the further prediction is a probability of the patient developing a co-morbid condition with their respiratory disorder.

Example 28. A method according to Example 27 (or any one of the preceding Examples), wherein the analysing comprises applying an event model to the data.

Example 29. A method according to Example 27 (or any one of the preceding Examples), wherein the action comprises issuing an alert to a healthcare provider.

Example 30. A method according to any of Examples 2 to 5 (or any one of the preceding Examples), wherein the therapy program comprises a setting of the respiratory pressure therapy device.

Example 31. A method according to Example 30 (or any one of the preceding Examples), wherein the adjustment to the therapy program comprises changing a setting of the respiratory pressure therapy device.

Example 32. A method according to any of Examples 1 to 31 (or any one of the preceding Examples), wherein the data relating to respiratory therapy delivered to the patient comprises electronic medical records of the patient.

Example 33. A method according to any of Examples 2 to 5 (or any one of the preceding Examples), wherein the therapy program comprises one or more of a model, type, and size of a patient interface through which the respiratory pressure therapy device delivers respiratory therapy to the patient.

Example 34. A method according to Example 33 (or any one of the preceding Examples), wherein the adjustment to the therapy program comprises a change to the patient interface.

Example 35. A method according to any of Examples 1 to 34 (or any one of the preceding Examples), wherein the data relating to respiratory therapy delivered to the patient comprises behavioural data indicating how the patient is interacting with the respiratory pressure therapy device.

Example 36. A method according to Example 3 (or any one of the preceding Examples), wherein the patient is associated with a patient computing device through which the engagement is configured to take place.

Example 37. A method according to Example 36 (or any one of the preceding Examples), wherein the data relating to respiratory therapy delivered to the patient comprises behavioural data indicating how the patient is interacting with the patient computing device.

Example 38. A method according to any of Examples 3 to 5 (or any one of the preceding Examples), wherein the adjustment comprises changing an engagement action of a rule of the engagement rule set.

Example 39. A method according to Example 38 (or any one of the preceding Examples), wherein the changing comprises changing a mode of an engagement action of a rule of the engagement rule set.

Example 40. A method according to any of Examples 3 to 5 (or any one of the preceding Examples), wherein an engagement action comprises a message to a partner or caregiver of the patient.

Example 41. A system for treating a respiratory disorder in a patient, the system comprising: a server configured to communicate with a respiratory pressure therapy device, the respiratory pressure therapy device configured to deliver respiratory therapy to the patient, the server comprising a processor configured to: analyse data relating to the respiratory therapy delivered to the patient via the respiratory pressure therapy device to generate data representing a compliance prediction about the progress of the respiratory therapy; select an action to improve the respiratory therapy based on the data representing the compliance prediction; and take or prompt the selected action to improve the respiratory therapy.

Example 42. A system according to Example 41 (or any one of the preceding Examples), wherein the respiratory therapy is CPAP therapy.

Example 43. A system according to any of Examples 41 to 42 (or any one of the preceding Examples), wherein the respiratory pressure therapy device is configured to deliver the respiratory therapy to the patient according to a therapy program comprising an engagement rule set specifying engagements with the patient.

Example 44. A system according to Example 43 (or any one of the preceding Examples), further comprising a patient computing device through which engagement with the patient is configured to take place.

Example 45. A system according to Example 44 (or any one of the preceding Examples), wherein the patient computing device is further configured to intermediate between the respiratory pressure therapy device and the server.

Example 46. A system according to Example 44 (or any one of the preceding Examples), further comprising one or more physiological sensors configured to provide physiological data of the patient.

Example 47. A system according to Example 46 (or any one of the preceding Examples), wherein the patient computing device is further configured to intermediate between the one or more physiological sensors and the server.

Example 48. A system according to Example 41 (or any one of the preceding Examples), further comprising a patient computing device configured to intermediate between the respiratory pressure therapy device and the server.

Example 49. A system according to any of Examples 41 to 48 (or any one of the preceding Examples), further comprising one or more physiological sensors configured to provide physiological data of the patient.

Example 50. A system according to Example 49 (or any one of the preceding Examples), further comprising a patient computing device configured to intermediate between the one or more physiological sensors and the server.

Example 51. The system according to any one of Examples 41 to 50 (or any one of the preceding Examples) further comprising one or more respiratory pressure therapy devices.

Example 52. A server comprising a processor configured to: analyse data relating to respiratory therapy delivered to a patient via a respiratory pressure therapy device to generate data in the processor representing a compliance prediction about the progress of the respiratory therapy; select an action to improve the respiratory therapy based on the data representing the compliance prediction; and take or prompt the selected action to improve the respiratory therapy.

Example 53. A system for monitoring patient compliance with respiratory pressure therapy, the system comprising: one or more processors configured to receive data concerning patient respiratory pressure therapy, the one or more processors further configured to: analyse usage data concerning the patient respiratory pressure therapy, the usage data concerning a period of days; generate compliance prediction indicators concerning the patient respiratory pressure therapy based on the analysis of usage data, the compliance prediction indicators representing whether compliance will be likely; and recommend engagement action to improve patient respiratory pressure therapy compliance based on evaluation of the compliance prediction indicators.

Example 54. A method of monitoring patient compliance with respiratory pressure therapy, the method comprising: analysing, in a processor, usage data concerning the patient respiratory pressure therapy, the usage data concerning a period of days; generating, with the processor, compliance prediction indicators concerning the patient respiratory pressure therapy based on the analysis of usage data, the compliance prediction indicators representing whether compliance will be likely; and recommending, with the processor, engagement action to improve patient respiratory pressure therapy compliance based on evaluation of the compliance prediction indicators.

Example 55. A server comprising a processor configured to: analyse usage data concerning the patient respiratory pressure therapy, the usage data concerning a period of days; generate compliance prediction indicators concerning the patient respiratory pressure therapy based on the analysis of usage data, the compliance prediction indicators representing whether compliance will be likely; and recommend engagement action to improve patient respiratory pressure therapy compliance based on evaluation of the compliance prediction indicators.

The invention claimed is:

1. A method of generating a therapy compliance prediction for a patient receiving respiratory therapy via a respiratory pressure therapy device, the method performed at least in part by a data server and comprising:
   receiving, by the data server over a communication network, therapy data captured by the respiratory pressure therapy device while providing therapy to the patient, the data server being located remotely from the patient and the respiratory pressure therapy device;
   receiving, by the data server, patient data from at least one of a patient computing device or a healthcare provider server, wherein each of the patient computing device and the healthcare provider server is located remotely from the data server;
   computing, by the data server, a current compliance prediction for the patient comprising a first success predictor score (SPS) value generated using the therapy data and the patient data, the first SPS value associated with a recent therapy session of the patient performed by the respiratory pressure therapy device, wherein the current compliance prediction is a prediction about a future compliance with the patient's respiratory therapy;
   accessing a second SPS value determined from a previous therapy session of the patient that was performed by the respiratory pressure therapy device;
   determining, by the data server based on the current compliance prediction, whether an action is needed to improve the patient's respiratory therapy, the determining comprising:
      comparing the first SPS value to at least one, or each, of a plurality of thresholds to determine whether the first SPS value is less than or equal to the at least one of the plurality of thresholds, wherein each of the plurality of thresholds is a value that represents a level of non-compliance risk with the patient's respiratory therapy, and
      comparing the first SPS value to the second SPS value to determine whether the first SPS value is less than or equal to the second SPS value, and wherein each of the first SPS value and the second SPS value represents a probability of a compliance with the patient's respiratory therapy;
   upon the data server determining that an action is needed based on results of the comparisons, selecting, by the data server, an action to improve the patient's respiratory therapy;
   transmitting, by the data server over the communication network, a notification to the patient computing device or the healthcare provider server prompting the selected action to improve the patient's respiratory therapy;
   transmitting control commands to adjust one or more settings of the respiratory pressure therapy device based on the determining; and
   controlling, by a controller of the respiratory pressure therapy device, operation of the respiratory pressure therapy device to provide a therapy in accordance with the adjusted one or more settings.

2. The method according to claim 1, wherein the respiratory therapy is in accordance with a therapy program, and the action is an adjustment to the therapy program.

3. The method according to claim 2, wherein the therapy program comprises an engagement rule set specifying details of engagement with the patient.

4. The method according to claim 3, wherein the action comprises adjusting aggressiveness of the engagement rule set.

5. The method according to claim 3, wherein determining whether an action is needed is based on a previously computed compliance prediction for the patient, wherein the previously computed compliance prediction comprises the second SPS.

6. The method according to claim 1, wherein the patient data comprises answers supplied by the patient to a questionnaire.

7. The method according to claim 1, wherein computing the current compliance prediction comprises applying a compliance model to a first numerical value representing the therapy data and a second numerical value representing the patient data, and the compliance prediction is the first SPS value indicating a probability that the patient will be compliant with a predetermined compliance rule.

8. The method according to claim 1, wherein computing the current compliance prediction comprises applying a weight to each of a first numerical value representing the therapy data and a second numerical value representing the patient data, and combining the weighted first numerical value and the weighted second numerical value in a linear sum.

9. The method according to claim 1, further comprising analyzing the therapy data to generate a further prediction, wherein the further prediction is a prediction of whether the patient will develop a co-morbid condition with their respiratory disorder, wherein the action comprises issuing an alert to this effect.

10. The method according to claim 2, wherein the therapy program comprises a setting of the respiratory pressure therapy device.

11. The method according to claim 10, wherein the adjustment to the therapy program comprises changing a setting of the respiratory pressure therapy device.

12. The method according to claim 2, wherein the therapy program comprises one or more of a model, type, and size of a patient interface through which the respiratory pressure therapy device delivers respiratory therapy to the patient.

13. The method according to claim 12, wherein the adjustment to the therapy program comprises a change to the patient interface.

14. The method according to claim 1, wherein the data relating to respiratory therapy delivered to the patient comprises behavioral data indicating how the patient is interacting with the respiratory pressure therapy device.

15. The method according to claim 3, wherein the patient is associated with a patient computing device through which the engagement is configured to take place.

16. The method according to claim 15, wherein the data relating to respiratory therapy delivered to the patient comprises behavioral data indicating how the patient is interacting with the patient computing device.

17. The method according to claim 3, wherein the action comprises adjusting an action portion of a rule of the engagement rule set.

18. The method according to claim 1, wherein the determining whether an action is needed to improve the patient's respiratory therapy further comprises retrieving a therapy compliance predictor for a plurality of therapy sessions for the patient.

19. The method according to claim 1 further comprising changing, by the respiratory pressure therapy device, the one or more settings of the respiratory pressure therapy device in accordance with the transmitted control commands.

20. A system for generating a therapy compliance prediction for a patient receiving respiratory therapy via a respiratory pressure therapy device, the system comprising:
(a) a data server configured to communicate with the respiratory pressure therapy device, the respiratory pressure therapy device configured to deliver respiratory therapy to the patient, the data server comprising one or more processors configured to:
receive therapy data captured by the respiratory pressure therapy device while respiratory therapy is being delivered to the patient via the respiratory pressure therapy device;
receive patient data from at least one of a patient computing device or a healthcare provider server, the patient computing device and the healthcare provider server each being located remotely from the data server;
access a second SPS value determined from a previous therapy session of the patient that was performed by the respiratory pressure therapy device;
compute a current compliance prediction for the patient comprising a first success predictor score (SPS) value generated using the therapy data and the patient data, the first SPS value associated with a recent therapy session of the patient performed by the respiratory pressure therapy device, wherein the current compliance prediction is a prediction about a future compliance with the patient's respiratory therapy;
determine whether an action is needed to improve the patient's respiratory therapy, the determination comprises:
compare the first SPS value to at least one, or each, of a plurality of thresholds to determine whether the first SPS value is less than or equal to the at least one of the plurality of thresholds, wherein each of the plurality of thresholds is a value that represents a level of non-compliance risk with the patient's respiratory therapy, and
compare the first SPS value to the second SPS value to determine whether the first SPS value is less than or equal to the second SPS value, and wherein each of the first SPS value and the second SPS value represents a probability of a compliance with the patient's respiratory therapy;
upon determination that an action is needed based on results of the comparisons, select an action to improve the patient's respiratory therapy;
transmit a notification to the patient computing device or the healthcare provider server prompting the selected action to improve the patient's respiratory therapy; and
transmit control commands to adjust one or more settings of the respiratory pressure therapy device based on the determining; and
(b) the respiratory pressure therapy device, wherein the respiratory pressure therapy device comprises a controller configured, by the adjusted one or more settings, to control operation of the respiratory pressure therapy device, and wherein the respiratory pressure therapy device is operable to provide a therapy to the patient in accordance with the adjusted one or more settings.

21. The system according to claim 20, wherein the respiratory therapy is Continuous Positive Airway Pressure (CPAP) therapy.

22. A data server comprising one or more processors configured to:
receive therapy data captured by a respiratory pressure therapy device while respiratory therapy is being delivered to a patient via the respiratory pressure therapy device;
receive patient data from at least one of a patient computing device or a healthcare provider server, the patient computing device and the healthcare provider server each being located remotely from the data server;
access a second SPS value determined from a previous therapy session of the patient that was performed by the respiratory pressure therapy device;
compute a current compliance prediction for the patient comprising a first success predictor score (SPS) value generated using the therapy data and the patient data, the first SPS value associated with a recent therapy session of the patient performed by the respiratory pressure therapy device, wherein the current compliance prediction is a prediction about a future compliance with the patient's respiratory therapy;
determine whether an action is needed to improve the patient's respiratory therapy, the determination comprises:
comparison of the first SPS value to at least one, or each, of a plurality of thresholds to determine whether the first SPS value is less than or equal to the at least one of the plurality of thresholds, wherein each of the plurality of thresholds is a value that: represents a level of non-compliance risk with the patient's respiratory therapy, and
comparison of the first SPS value to the second SPS value to determine whether the first SPS value is less than or equal to the second SPS value, and wherein each of the first SPS value and the second SPS value represents a probability of a compliance with the patient's respiratory therapy;
upon determination that an action is needed based on results of the comparisons, select an action to improve the patient's respiratory therapy;
transmit a notification to the patient computing device or the healthcare provider server prompting the selected action to improve the patient's respiratory therapy; and
transmit control commands to the respiratory pressure therapy device to adjust one or more settings of the respiratory pressure therapy device based on the determining, whereby the transmission of the control commands to the respiratory pressure therapy device enables, by remote control, the respiratory pressure therapy device to provide a therapy in accordance with the adjusted one or more settings, and whereby the respiratory pressure therapy device receives the control commands and adjusts the one or more settings of the respiratory pressure therapy device and is operable to provide therapy to the patient in accordance with the adjusted one or more settings.

\* \* \* \* \*